United States Patent [19]

Chandler

[11] Patent Number: 5,468,648
[45] Date of Patent: Nov. 21, 1995

[54] INTERRUPTED-FLOW ASSAY DEVICE

[75] Inventor: Howard M. Chandler, Yarmouth, Me.

[73] Assignee: SmithKline Diagnostics, Inc., San Jose, Calif.

[21] Appl. No.: 163,341

[22] Filed: Dec. 7, 1993

Related U.S. Application Data

[63] Continuation-in-part of Ser. No. 40,430, Mar. 31, 1993, which is a continuation-in-part of Ser. No. 888,831, May 27, 1992, abandoned, which is a continuation-in-part of Ser. No. 706,639, May 29, 1991.

[51] Int. Cl.⁶ ............................................ G01N 33/543
[52] U.S. Cl. ................ 436/518; 422/58; 422/60; 435/7.1; 435/7.92; 435/7.93; 435/7.94; 435/7.95; 435/970; 435/973; 435/974; 436/514; 436/530; 436/525; 436/538; 436/540; 436/807; 436/810
[58] Field of Search ..................... 422/56–60; 435/7.1, 435/5, 6, 7.92–7.95, 970, 973, 974; 436/514, 518, 530, 525, 538, 540, 807, 810

[56] References Cited

U.S. PATENT DOCUMENTS

| | | | |
|---|---|---|---|
| 3,723,064 | 3/1973 | Liotta | 23/230 R |
| 3,798,004 | 3/1974 | Zerachia et al. | 23/253 TP |
| 3,888,629 | 6/1975 | Bagshawe | 23/230 B |
| 3,915,647 | 10/1975 | Wright | 23/253 TP |
| 3,933,594 | 1/1976 | Mulligan | 195/103.5 R |
| 3,966,897 | 6/1976 | Renn et al. | 424/1.5 |
| 3,985,867 | 10/1976 | Redshaw | 424/1.5 |
| 3,990,850 | 11/1976 | Friedman et al. | 23/230 B |
| 3,993,451 | 11/1976 | Verbeck | 23/253 TP |
| 3,996,006 | 12/1976 | Pagano | 23/253 |
| 4,018,662 | 4/1977 | Ruhenstroth-Bauer et al. | 204/299 R |
| 4,094,647 | 6/1978 | Deutsch et al. | 23/253 TP |
| 4,108,729 | 8/1978 | Mennen | 195/127 |
| 4,110,079 | 8/1978 | Schaeffer | 23/253 TP |
| 4,168,146 | 9/1979 | Grubb et al. | 23/230 B |

(List continued on next page.)

FOREIGN PATENT DOCUMENTS

| | | |
|---|---|---|
| 0063810 | 11/1982 | European Pat. Off. |
| 0183442 | 6/1986 | European Pat. Off. |
| 0191640 | 8/1986 | European Pat. Off. |
| 0225054 | 6/1987 | European Pat. Off. |
| 0238012 | 9/1987 | European Pat. Off. |
| 0250137 | 12/1987 | European Pat. Off. |
| 0262328 | 4/1988 | European Pat. Off. |
| 0269876 | 6/1988 | European Pat. Off. |
| 0323605 | 7/1988 | European Pat. Off. |

(List continued on next page.)

OTHER PUBLICATIONS

T. C. J. Gribnau et al., "Particle–Labelled Immunoassays: A Review," *J. Chromatograph.* 376:175–189 (1986) (Exhibit 186).

*Primary Examiner*—Carol A. Spiegel
*Attorney, Agent, or Firm*—Merchant, Gould, Smith, Edell, Welter & Schmidt

[57] ABSTRACT

The present invention provides chromatographic assay devices that can perform multiple assays simultaneously in the same test strip, as well as methods for their use. One of the assays can be an immunological assay to detect an antigen, such as human chorionic gonadotropin, while another assay can be a serological assay to detect an antibody, such as anti-rubella antibody. An assay device according to the present invention can comprise: (1) a first opposable component including at least one chromatographic medium having a specific binding partner to the first analyte and a specific binding partner to the second analyte immobilized thereto in separate, discrete, non-overlapping zones; and (2) a second opposable component including an absorber. The first and second opposable components are configured such that bringing the first and second opposable components into opposition causes the absorber to come into operable contact with at least one chromatographic medium so that the zone containing the specific binding partner to the first analyte is functionally divided from the zone containing the specific binding partner to the second analyte so that both analytes can be detected.

25 Claims, 2 Drawing Sheets

U.S. PATENT DOCUMENTS

| | | | |
|---|---|---|---|
| 4,189,304 | 2/1980 | Adams, Jr. et al. | 23/230 B |
| 4,223,089 | 9/1980 | Rothe et al. | 435/12 |
| 4,246,339 | 1/1981 | Cole et al. | 435/7 |
| 4,299,916 | 11/1981 | Litman et al. | 435/6 |
| 4,313,734 | 2/1982 | Leuvering | 422/61 X |
| 4,333,733 | 6/1982 | Sanford et al. | 23/230 B |
| 4,365,970 | 12/1982 | Lawrence et al. | 436/66 |
| 4,366,241 | 12/1982 | Tom et al. | 435/7 |
| 4,376,110 | 3/1983 | David et al. | 436/513 |
| 4,391,904 | 7/1983 | Litman et al. | 435/7.9 |
| 4,425,438 | 1/1984 | Bauman et al. | 436/527 |
| 4,427,769 | 1/1984 | Adlecreutz et al. | 435/7 |
| 4,435,504 | 3/1984 | Zuk et al. | 435/7.9 |
| 4,442,204 | 4/1984 | Greenquist et al. | 435/7.9 |
| 4,444,193 | 4/1984 | Fogt et al. | 128/632 |
| 4,446,232 | 5/1984 | Liotta | 435/7.9 |
| 4,447,526 | 5/1984 | Rupchock et al. | 435/7.9 |
| 4,447,529 | 5/1984 | Greenquist et al. | 435/7.9 |
| 4,459,358 | 7/1984 | Berke | 436/170 |
| 4,461,829 | 7/1984 | Greenquist | 435/7.9 |
| 4,474,878 | 10/1984 | Halbert et al. | 435/7.9 |
| 4,477,575 | 10/1984 | Vogel et al. | 436/170 |
| 4,517,288 | 5/1985 | Giegel et al. | 435/7.9 |
| 4,533,629 | 8/1985 | Litman et al. | 435/7.9 |
| 4,582,811 | 4/1986 | Pucci et al. | 436/548 |
| 4,594,327 | 6/1986 | Zuk | 436/514 |
| 4,623,461 | 11/1986 | Hossom et al. | 210/445 |
| 4,629,690 | 12/1986 | Weng et al. | 435/7.9 |
| 4,642,285 | 2/1987 | Halbert et al. | 435/7.9 |
| 4,668,619 | 5/1987 | Greenquist et al. | 435/7.9 |
| 4,678,757 | 7/1987 | Rapkin et al. | 436/169 |
| 4,683,197 | 7/1987 | Gallati | 435/28 |
| 4,690,907 | 9/1987 | Hibino et al. | 436/514 |
| 4,693,834 | 9/1987 | Hossom | 210/767 |
| 4,703,017 | 10/1987 | Campbell et al. | 436/501 |
| 4,717,656 | 1/1988 | Swanljung | 422/58 X |
| 4,738,823 | 4/1988 | Engelmann | 422/56 |
| 4,740,468 | 4/1988 | Weng et al. | 435/7.9 |
| 4,752,562 | 6/1988 | Sheiman et al. | 45/5 |
| 4,761,381 | 8/1988 | Blatt et al. | 436/165 |
| 4,775,636 | 10/1988 | Moeremans et al. | 436/518 |
| 4,780,280 | 10/1988 | Berger et al. | 422/56 |
| 4,786,594 | 11/1988 | Khanna et al. | 435/7.9 |
| 4,789,526 | 12/1988 | Matkovich | 422/101 |
| 4,789,629 | 12/1988 | Baker et al. | 435/7.9 |
| 4,790,979 | 12/1988 | Terminiello et al. | 422/56 |
| 4,797,260 | 1/1989 | Parker | 422/101 |
| 4,803,170 | 2/1989 | Stanton et al. | 436/518 |
| 4,806,311 | 2/1989 | Greenquist | 422/56 |
| 4,806,312 | 2/1989 | Greenquist | 422/56 |
| 4,810,470 | 3/1989 | Burkhardt et al. | 422/56 |
| 4,814,142 | 3/1989 | Gleisner | 422/56 |
| 4,816,224 | 3/1989 | Vogel et al. | 422/55 |
| 4,818,677 | 4/1989 | Hay-Kaufman et al. | 435/4 |
| 4,826,759 | 5/1989 | Guire et al. | 435/4 |
| 4,837,373 | 6/1989 | Gunkel et al. | 422/56 |
| 4,837,395 | 6/1989 | Leeder et al. | 435/7.9 |
| 4,843,000 | 6/1989 | Litman et al. | 435/7.9 |
| 4,853,335 | 8/1989 | Olsen et al. | 436/527 |
| 4,855,240 | 8/1989 | Rosenstein et al. | 436/514 |
| 4,857,453 | 8/1989 | Ullman et al. | 435/7.9 |
| 4,859,612 | 8/1989 | Cole et al. | 436/523 |
| 4,861,711 | 8/1989 | Friesen et al. | 436/7.9 |
| 4,868,108 | 9/1989 | Bahar et al. | 435/7.9 |
| 4,876,067 | 10/1989 | Deneke et al. | 422/56 |
| 4,877,586 | 10/1989 | Devaney, Jr. et al. | 422/101 |
| 4,879,215 | 11/1989 | Weng et al. | 435/7.9 |
| 4,883,764 | 11/1989 | Kloepfer | 436/63 |
| 4,900,663 | 2/1990 | Wie et al. | 422/56 X |
| 4,912,034 | 3/1990 | Kalra et al. | 435/7.9 |
| 4,916,056 | 4/1990 | Brown, III et al. | 435/7.9 |
| 4,916,078 | 4/1990 | Klose et al. | 436/165 |
| 4,918,025 | 4/1990 | Grenner | 436/165 |
| 4,920,046 | 4/1990 | McFarland et al. | 436/528 X |
| 4,938,927 | 7/1990 | Kelton et al. | 422/64 |
| 4,939,098 | 7/1990 | Suzuki et al. | 436/514 |
| 4,943,522 | 7/1990 | Eisinger et al. | 435/7.9 |
| 4,952,517 | 8/1990 | Bahar | 436/518 |
| 4,956,275 | 9/1990 | Zuk et al. | 435/7.9 |
| 4,956,302 | 9/1990 | Gordon et al. | 436/161 |
| 4,959,307 | 9/1990 | Olson | 435/7.9 |
| 4,960,691 | 10/1990 | Gordon et al. | 435/6 |
| 4,963,325 | 10/1990 | Lennon et al. | 422/61 |
| 4,963,468 | 10/1990 | Olson | 435/7.9 |
| 4,977,078 | 12/1990 | Niimura et al. | 435/7.4 |
| 4,981,786 | 1/1991 | Dafforn et al. | 435/7.9 |
| 4,999,285 | 3/1991 | Stiso | 435/7.9 |
| 4,999,287 | 3/1991 | Allen et al. | 435/11 |
| 5,006,464 | 4/1991 | Chu et al. | 435/7.1 |
| 5,006,474 | 4/1991 | Horstman et al. | 422/57 X |
| 5,017,009 | 5/1991 | Schutt et al. | 358/338 |
| 5,030,555 | 7/1991 | Clemmons | 435/5 |
| 5,030,558 | 7/1991 | Litman et al. | 435/7.91 |
| 5,039,607 | 8/1991 | Skold et al. | 435/7.5 |
| 5,051,237 | 9/1991 | Grenner et al. | 422/56 |
| 5,071,746 | 12/1991 | Wilk et al. | 435/7.94 |
| 5,073,484 | 12/1991 | Swanson et al. | 435/7.92 |
| 5,075,078 | 12/1991 | Osikowicz et al. | 422/56 |
| 5,079,142 | 1/1992 | Coleman et al. | 435/7.92 |
| 5,079,174 | 1/1992 | Buck et al. | 436/548 |
| 5,085,987 | 2/1992 | Olson | 435/7.91 |
| 5,085,988 | 2/1992 | Olson | 435/7.91 |
| 5,096,809 | 3/1992 | Chen et al. | 435/7.9 |
| 5,100,619 | 3/1992 | Baker et al. | 422/58 |
| 5,104,811 | 4/1992 | Berger et al. | 436/164 |
| 5,104,812 | 4/1992 | Kurn et al. | 436/165 |
| 5,106,582 | 4/1992 | Baker | 422/58 |
| 5,106,758 | 4/1992 | Adler et al. | 436/165 |
| 5,110,550 | 5/1992 | Schlipfenbacher et al. | 422/56 |
| 5,114,673 | 5/1992 | Berger et al. | 422/56 |
| 5,114,862 | 5/1992 | Brenneman | 436/169 |
| 5,120,643 | 6/1992 | Ching et al. | 435/7.92 |
| 5,120,662 | 6/1992 | Chan et al. | 436/530 |
| 5,132,208 | 7/1992 | Freitag et al. | 435/7.1 |
| 5,135,872 | 8/1992 | Pouletty et al. | 436/180 |
| 5,135,873 | 8/1992 | Patel et al. | 436/180 |
| 5,137,804 | 8/1992 | Greene et al. | 435/5 |
| 5,137,808 | 8/1992 | Ullman et al. | 435/7.9 |
| 5,141,850 | 8/1992 | Cole et al. | 436/525 |
| 5,156,952 | 10/1992 | Litman et al. | 435/7.91 |
| 5,158,869 | 10/1992 | Pouletty et al. | 435/7.9 |
| 5,160,486 | 11/1992 | Schlipfenbacher et al. | 422/56 |
| 5,162,237 | 11/1992 | Messenger et al. | 436/523 |
| 5,164,294 | 11/1992 | Skold et al. | 435/7.5 |
| 5,177,021 | 1/1993 | Kondo | 436/518 |
| 5,182,191 | 1/1993 | Fan et al. | 435/7.9 |
| 5,185,127 | 2/1993 | Vonk | 422/56 |
| 5,188,939 | 2/1993 | Mangold et al. | 435/7.92 |
| 5,188,966 | 2/1993 | Eikmeier et al. | 436/170 |
| 5,202,267 | 4/1993 | Ditlow et al. | 436/525 |
| 5,202,268 | 4/1993 | Kuhn et al. | 436/525 |
| 5,209,904 | 5/1993 | Forney et al. | 422/73 |
| 5,223,436 | 6/1993 | Freitag et al. | 436/97 |
| 5,234,813 | 8/1993 | McGeehan et al. | 435/7.9 |
| 5,248,619 | 9/1993 | Skold et al. | 436/514 |
| 5,256,372 | 10/1993 | Brooks et al. | 422/58 |
| 5,258,163 | 11/1993 | Krause et al. | 422/58 |
| 5,260,193 | 11/1993 | Olson | 435/7.91 |
| 5,260,222 | 11/1993 | Patel et al. | 436/180 |
| 5,264,180 | 11/1993 | Allen et al. | 422/56 |
| 5,275,785 | 1/1994 | May et al. | 422/56 |
| 5,278,079 | 1/1994 | Gubinski et al. | 436/165 |

| | | | |
|---|---|---|---|
| 5,308,580 | 5/1994 | Clark | 422/58 |
| 5,314,804 | 5/1994 | Boguslaski et al. | 435/12 |

FOREIGN PATENT DOCUMENTS

| | | |
|---|---|---|
| 0279097 | 8/1988 | European Pat. Off. . |
| 0284232 | 9/1988 | European Pat. Off. . |
| 0291194 | 11/1988 | European Pat. Off. . |
| 0296724 | 12/1988 | European Pat. Off. . |
| 0297292 | 1/1989 | European Pat. Off. . |
| 0299428 | 1/1989 | European Pat. Off. . |
| 0306772 | 3/1989 | European Pat. Off. . |
| 0310406 | 4/1989 | European Pat. Off. . |
| 0319294 | 6/1989 | European Pat. Off. . |
| 0322340 | 6/1989 | European Pat. Off. . |
| 0415679 | 3/1991 | European Pat. Off. . |
| 0443231 | 8/1991 | European Pat. Off. . |
| 0516095 | 5/1992 | European Pat. Off. . |
| 0560410 | 9/1993 | European Pat. Off. . |
| 2016687 | 9/1979 | United Kingdom . |
| 2204398 | 9/1988 | United Kingdom 422/56 |
| WO89/03992 | 5/1989 | WIPO . |
| WO90/5906 | 5/1990 | WIPO . |
| WO91/01003 | 1/1991 | WIPO . |
| WO91/19980 | 12/1991 | WIPO . |
| WO92/01226 | 1/1992 | WIPO . |

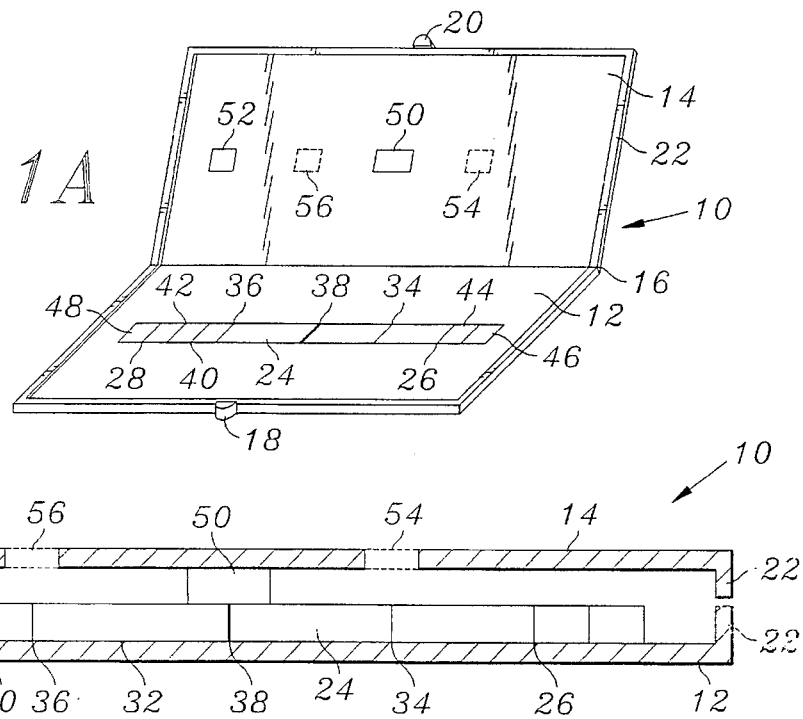
FIG. 1A
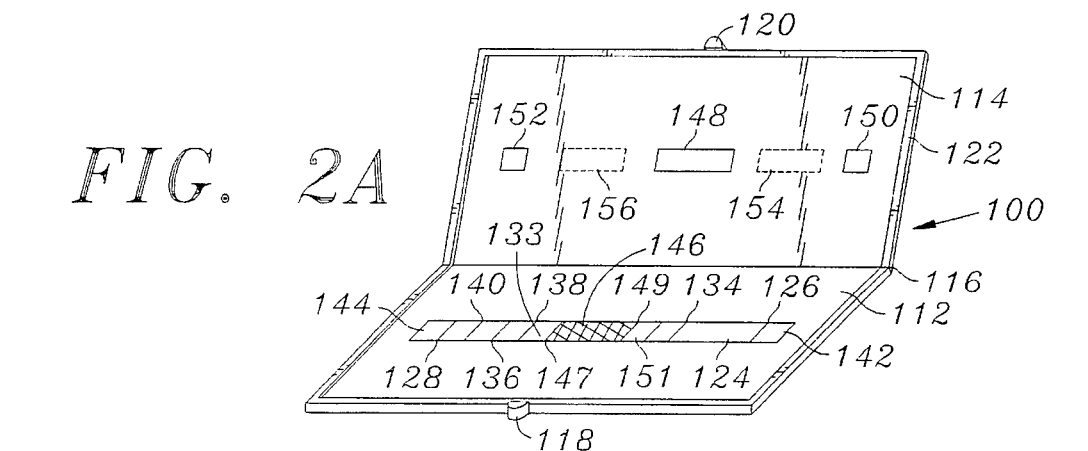
FIG. 1B
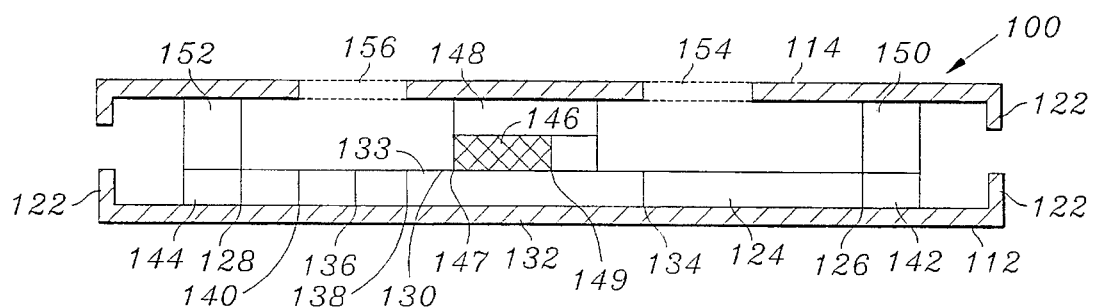
FIG. 2A
FIG. 2B

INTERRUPTED-FLOW ASSAY DEVICE

CROSS-REFERENCES

This application is a continuation-in-part of U.S. application Ser. No. 08/040,430, by Howard M. Chandler, Roger N. Piasio, and Karen Prouty, filed Mar. 31, 1993, and entitled "Assay Device," which was a continuation-in-part of U.S. application Ser. No. 07/888,831, by Howard M. Chandler, filed May 27, 1992, and also entitled "Assay Device," now abandoned which was in turn a continuation-in-part of U.S. application Ser. No. 07/706,639 by Howard M. Chandler, filed May 29, 1991, entitled "Assay Device." All three of these preceding applications are incorporated herein in their entirety by this reference.

TABLE OF CONTENTS

For convenience, the following Table of Contents is Provided:
BACKGROUND OF THE INVENTION
SUMMARY
BRIEF DESCRIPTION OF THE DRAWINGS
DESCRIPTION
Definitions
I. PRINCIPLES OF OPERATION OF INTERRUPTED-FLOW ASSAY DEVICES
    A. Principles of Operation
    B. Elements Common to Devices According to the Present Invention
        1. The Chromatographic Medium
        2. Absorbers
        3. Other Fluid-Carrying Elements
        4. Opposable Components
II. ASSAY DEVICES
    A. Device with Undivided Chromatographic Medium Employing Uninterrupted Flow in One Direction
        1. Device with Sample Preparation Zone in Operable Contact with Chromatographic Medium
        2. Device with Sample Preparation Zone Interrupting Chromatographic Medium
III. ANALYTES, SPECIFIC BINDING PARTNERS, AND LABELS
    A. Analytes
    B. Specific Binding Partners
    C. Labels
Example—Interrupted-Flow Assay Device for Detection of Rubella and Human Chorionic Gonadotropin ADVANTAGES OF THE INVENTION

BACKGROUND OF THE INVENTION

This invention is directed to test devices for determination of characteristics of samples, unitized housings, and kits incorporating the test strips and housings, and methods of determining the characteristics of samples using the test strips and housings.

Among the many analytical systems used for detection and/or determination of analytes, particularly analytes of biological interest, are chromatographic assay systems. Among the analytes frequently assayed with such systems are: (1) hormones, such as human chorionic gonadotropin (hCG), frequently assayed as a marker of human pregnancy; (2) antigens, particularly antigens specific to bacterial, viral, and protozoan pathogens, such as Streptococcus, hepatitis virus, Giardia, and feline leukemia virus (FeLV); (3) antibodies, particularly antibodies induced as a result of infection with pathogens, such as antibody to the bacterium *Helicobacter pylori*, to human immunodeficiency virus (HIV), or to feline immunodeficiency virus (FIV); (4) other proteins, such as hemoglobin, frequently assayed in determinations of fecal occult blood, an early indicator of gastrointestinal disorders such as colon cancer; (5) enzymes, such as aspartate aminotransferase, lactate dehydrogenase, alkaline phosphatase, and glutamate dehydrogenase, frequently assayed as indicators of physiological function and tissue damage; (6) drugs, both therapeutic drugs such as antibiotics, tranquilizers, and anticonvulsants, and illegal drugs of abuse, such as cocaine, heroin, and marijuana; (7) environmental pollutants such as pesticides and aromatic hydrocarbons; and (8) vitamins.

Such chromatographic systems are frequently used by physicians, veterinarians, and medical technicians for rapid in-office diagnosis and therapeutic monitoring of a variety of conditions and disorders. They are also increasingly used by patients and animal owners themselves for at-home monitoring of such conditions and disorders.

Among the most important of such systems are the "thin layer" systems in which a solvent moves across a thin, flat, absorbent medium. Among the most important of tests that can be performed with such thin layer systems are immunoassays, which depend on the specific interaction between an antigen or hapten and a corresponding antibody. The use of immunoassays as a means of testing for the presence and/or amount of clinically important molecules has been known for some time. As early as 1956, J. M. Singer reported the use of an immune-based latex agglutination test for detecting a factor associated with rheumatoid arthritis (Singer et al., *Am.J. Med.* 22:888–892 (1956)).

Among the chromatographic techniques used in conjunction with immunoassays is a procedure known as immunochromatography. In general, this technique uses a disclosing reagent or particle that has been linked to an antibody to the molecule to be assayed, forming a conjugate. This conjugate is then mixed with a specimen, and if the molecule to be assayed is present in the specimen, the disclosing reagent-linked antibodies bind to the molecule to be assayed, thereby giving an indication that the molecule to be assayed is present. The disclosing reagent or particle can be identifiable by color, magnetic properties, radioactivity, emission of light, specific reactivity with another molecule, or another physical or chemical property. The specific reactions that are employed vary with the nature of the molecule being assayed and the sample to be tested.

Immunochromatographic assays fall into two principal categories: "sandwich" and "competitive," according to the nature of the antigen-antibody complex to be detected and the sequence of reactions required to produce that complex. The antigen to be detected can itself be an antibody, such as in serological assays for *H. pylori*-specific antibody or for antibody to FIV. In such cases, the antibody to be detected can be bound to a specific antigen. Alternatively, the antigen to be detected can be detected indirectly by using a labeled second antibody that binds the first antibody to the analyte to be detected.

In general, the sandwich immunochromatographic procedures call for mixing the sample that may contain the analyte to be assayed with antibodies to the analyte. The antibodies are mobile and typically are linked to a label or a disclosing agent, such as dyed latex, a colloidal metal sol, or a radioisotope. This mixture is then applied to a chromatographic medium containing a band or zone of immobilized antibody to the analyte of interest. The chromatographic medium is often in a form of a strip resembling a dipstick. When the complex of the molecule to be assayed and the labeled antibody reaches the zone of the immobilized antibodies on the chromatographic medium, binding occurs, and the bound labeled antibodies are localized at the zone. This indicates the presence of the molecule to be assayed. This technique can be used to obtain quantitative or semi-quantitative results.

Examples of sandwich immunoassays performed on test strips are described by U.S. Pat. No. 4,168,146 to Grubb et al. and U.S. Pat. No. 4,366,241 to Tom et al., both of which are incorporated herein by this reference.

In competitive immunoassays, the label is typically a labeled analyte or analyte analog which competes for binding of an antibody with any unlabeled analyte present in the sample. Competitive immunoassays are typically used for detection of analytes such as haptens, each hapten being monovalent and capable of binding only one antibody molecule. Examples of competitive immunoassay devices are those disclosed by U.S. Pat. No. 4,235,601 to Deutsch et al., U.S. Pat. No. 4,442,204 to Liotta, and U.S. Pat. No. 5,208,535 to Buechler et al., all of which are incorporated herein by this reference.

Although useful, currently available chromatographic techniques using test strips have a number of drawbacks. Many samples, such as fecal samples, contain particulate matter that can clog the pores of the chromatographic medium, greatly hindering the immunochromatographic process. Other samples, such as blood, contain cells and colored components that make it difficult to read the test. Even if the sample does not create interference, it is frequently difficult with existing chromatograph test devices to apply the sample uniformly to the chromatographic medium. This is highly desirable to ensure that the sample front moves uniformly through the chromatographic medium to insure that the sample reaches the area where binding is to occur in a uniform, straight-line matter. Other problems exist with currently-available test strips because of the nature of the sample to be assayed or the assay to be carried out. In many currently-available test strips, the time of passage of the specimen, from the point of application to passage past the specific capture band on the solid phase, frequently results in an undesirable time delay in obtaining results. In addition, variable specimen and reagents may be lost in the dead volume of the elements in the path to the capture zone.

With currently-available designs, it is also impractical to perform washing steps which are frequently desirable to improve sensitivity and reduce background. Also, it is difficult, and in many cases impossible, to carry out preincubation steps within the device.

Sample preparation and waste generation are responsible for other problems with currently available devices and techniques for immunochromatography. The increased prevalence of diseases spread by infected blood and blood fractions, such as AIDS and hepatitis, has exacerbated these problems. It is rarely possible to apply a sample (such as feces) or a sampling device (such as a throat swab) directly to the chromatographic medium. Several extraction and pretreatment reactions are usually required before the sample can be applied to the chromatographic medium. These reactions are typically carried out by the physician, veterinarian, or technicians performing the test in several small vessels, such as test tubes or microfuge tubes requiring the use of transfer devices such as pipettes. Each of these devices is then contaminated and must be disposed of using special precautions so that workers or people who may inadvertently come into contact with the waste do not become contaminated.

Still another limitation in chromatographic devices currently available for use by the physician, veterinarian, or technician is their inability to perform two-directional or two-dimensional chromatography. These techniques have long been known to be powerful analytical tools, but their complexity relative to simple unidirectional chromatography has made it difficult to apply them to test strip devices in the physician's office or a clinical laboratory.

Additionally, currently available test devices cannot perform two independent assays for two different analytes on the same test strip. One particular application of this would be the ability to perform a unidirectional sandwich assay and a bidirectional serological assay for an antibody as an analyte in the same test strip. Because the antibody that binds to a particular antigen is only a small fraction of the total antibody molecules present in the serum, the use of a unidirectional assay for an analyte that is an antibody is generally unsatisfactory, because the detection reagent will bind to many other antibody molecules on the test strip other than the antibody for the desired antigen, thus creating an unacceptably high background. This is true even if a second antibody specific for a class or subclass is used, because many individual antibodies belong to that class or subclass.

The ability to perform two such immunoassays on the single test strip is desirable when it is desired to determine the existence or non-existence of two specific diseases or conditions in the same sample. Alternatively, it can be desirable to perform assays for the simultaneous detection of both an antigen that is associated with a viral or bacterial pathogen and an antibody that is associated with the immunological response of the body to that pathogen in the same sample. An example is HIV virus, where a protein antigen known as p24 can be found in infected patients, while an antibody to the virus can also be found in many patients. It can be desirable to assay both of these in order to help determine the clinical status of the patient.

Accordingly, there is a need for an improved assay device capable of handling a broad range of chromatographic assays, including the ability to assay for two separate analytes in the same test strip. Such a device should be capable of receiving a possibly contaminated sample or a sample preparation device directly so as to eliminate the need for extraction vessels and transfer devices. Such a device, preferably in the form of a test strip, should also be capable of performing immunochromatographic assays on colored samples or samples containing particulates without interference and should be able to deliver the sample to the chromatographic medium uniformly and evenly to improve accuracy and precision of the tests. Moreover, such a test strip should minimize the time delay experienced in the performance of the assay and also minimize the dead volume in order to provide maximum economy in the use of samples and reagents.

SUMMARY

An assay device according to the present invention can perform at least two assays on the same test strip simultaneously, an immunological assay for detection of an antigen and a serological assay for detection of an antibody.

In general, such a device can comprise:

(1) a first opposable component including at least one chromatographic medium having a specific binding partner to the first analyte and a specific binding partner to the second analyte immobilized thereto in separate, discrete, non-overlapping zones; and (2) a second opposable component including an absorber.

The first and second opposable components are configured such that bringing the first and second opposable components into opposition causes the absorber to come into operable contact with at least one chromatographic medium. This results in the zone containing the specific binding partner to the first analyte being functionally divided from the zone containing the specific binding partner to the second analyte so that both analytes can be detected.

Typically, detection of the first analyte occurs by the formation of a ternary complex involving the first analyte, a labeled specific binding partner to the first analyte, and the immobilized specific binding partner to the first analyte. Detection of the second analyte occurs by formation of a ternary complex involving the second analyte, a detection reagent for the second analyte, and the immobilized specific binding partner to the second analyte.

The first analyte can be an antigen, while the second analyte can be an antibody.

The chromatographic medium can be divided into two sectors, a first sector containing the specific binding partner to the first analyte and a second sector containing the specific binding partner to the second analyte.

The second opposable component can further include at least one applicator. The second opposable component can include two applicators, an applicator containing a labeled specific binding partner for the first analyte and an applicator containing a detection reagent for the second analyte. The first and second opposable components can be configured such that when the first and second opposable components are brought into opposition, the absorber is in operable contact with the chromatographic medium such that the device performs a unidirectional chromatographic specific binding assay for the first analyte and a bidirectional chromatographic specific binding assay for the second analyte.

A first embodiment of an assay device according to the present invention can comprise:

(1) a first opposable component including:
  (a) a chromatographic medium having thereon in discrete, separated, non-overlapping zones:
    (i) a specific binding partner for a first analyte; and
    (ii) a specific binding partner for a second analyte; and
  (b) a first applicator to apply a sample and a labeled specific binding partner to the first analyte to the chromatographic medium; and (2) a second opposable component including:
  (a) a second applicator to apply a detection reagent for the second analyte to the chromatographic medium; and
  (b) an absorber, which, when the first and second opposable components are brought into opposition, is in operable contact with the chromatographic medium and functionally divides the chromatographic medium into two sectors, a first sector for the detection of the first analyte and a second sector for the detection of the second analyte.

In this device, the chromatographic medium can have a first end and a second end. The chromatographic medium can further include a conjugate zone containing a specific binding partner to the first analyte labeled with a first detectable label, with the conjugate zone being in operable contact with the first end of the chromatographic medium.

The first opposable component can also include a first applicator and a conductor. The first applicator is in operable contact with the conjugate zone, the conjugate zone bridging the first applicator and the first end of the chromatographic medium. The conductor is in operable contact with the second end of the chromatographic medium.

The second applicator can be separated from the absorber and can contain a detection reagent for the second analyte in a form that can be resolubilized by the addition of an aqueous liquid to the second applicator. The first and second opposable components can be configured so that bringing the first and second opposable components into opposition: (1) causes the second applicator to come into contact with the conductor; and (2) causes the absorber to come into contact with the chromatographic medium at a point between the specific binding partner for the first analyte and the specific binding partner for the second analyte. This causes the absorber to draw fluid from the first applicator through a portion of the chromatographic medium from the first end of the chromatographic medium to the specific binding partner for the first analyte and to draw fluid from the second applicator through a portion of the chromatographic medium from the second end of the chromatographic medium to the specific binding partner for the second analyte.

The second analyte can be an antibody produced by a mammalian species in response to an antigen. In this case, the detection reagent for the second analyte can include a labeled antibody that binds the second analyte on the basis of a specificity unrelated to the specificity by which the second analyte binds its corresponding antigen. This specificity can be species specificity. An example of the detection reagent is goat anti-human immunoglobulin G when the second analyte is a human IgG.

The chromatographic medium can include two sectors of differing porosities, a first sector including the specific binding partner for the first analyte and having a porosity suitable for the detection of the first analyte as an antigen and a second sector including the specific binding partner for the second analyte as an antibody and having a porosity suitable for the detection of the analyte as an antibody in a serological sample. A suitable material for the chromatographic medium is nitrocellulose.

A method for the detection and/or determination of at least two analytes in an aqueous sample, using this assay device, comprises the steps of:

(1) applying a first aliquot of the sample to the first applicator of the assay device;

(2) allowing the sample to migrate from the first applicator through the conjugate zone and then through at least the portion of the chromatographic medium including the specific binding partner for the first analyte;

(3) bringing the first and second opposable components into opposition to cause the second applicator to come into contact with the conductor and to cause the absorber to come into contact with the chromatographic medium to draw fluid from the conductor through the portion of the chromatographic medium including the specific binding partner for the second analyte from the conductor to the absorber; and (4) detecting and/or determining the two analytes in the test sample by observing and/or measuring the labeled specific binding partner to the first analyte bound at the specific binding partner for the first analyte immobilized on the chromatographic medium and the detection reagent for the second analyte bound to the specific binding partner for the second analyte immobilized on the chromatographic medium.

The labeled specific binding partner for the first analyte and the detection reagent for the second analyte can be each labeled with a visually detectable label. In this case, the step of observing and/or measuring the labeled specific binding partner for the first analyte and the detection reagent for the second analyte is performed visually.

A second embodiment of an assay device according to the present invention has a sample preparation zone that separates the specific binding partner for the first analyte and the specific binding partner for the second analyte on the at least one chromatographic medium. This embodiment comprises:

(1) a first opposable component including:
  (a) at least one chromatographic medium having thereon in discrete, separated, non-overlapping zones:
    (i) a specific binding partner for a first analyte; and
    (ii) a specific binding partner for a second analyte;
  (b) a sample preparation zone separating the specific binding partner for the first analyte and the specific binding partner for the second analyte on the at least one chromatographic medium; and
(2) a second opposable component including:
  (a) an absorber;
  (b) a first applicator; and
  (c) a second applicator.

In this embodiment, the first and second opposable components are configured such that when the first and second opposable components are brought into opposition: (1) the first applicator applies a labeled specific binding partner for the first analyte to the first zone of the chromatographic medium; (2) the second applicator applies a detection reagent for the second analyte to the second zone of the chromatographic medium; and (3) the absorber functionally divides the first zone from the second zone so that the labeled specific binding partner to the first analyte is substantially excluded from the second zone and the detection reagent for the second analyte is substantially excluded from the first zone.

In one version of this embodiment, the first opposable component further includes a first conductor in operable contact with the first end of the chromatographic medium and a second conductor in operable contact with the second end of the chromatographic medium. On the second opposable component, the first applicator is separated from the absorber and contains a specific binding partner to the first analyte labeled with a detectable label in a form that can be resolubilized by the addition of an aqueous liquid to the first applicator. The second applicator is separated from the absorber and contains a detection reagent for the second analyte in a form that can be resolubilized by the addition of an aqueous liquid to the second applicator.

This version comprises:

(1) a first opposable component including:
  (a) a chromatographic medium having a first end and a second end, the chromatographic medium having thereon in discrete, separated, non-overlapping zones:
    (i) a specific binding partner for a first analyte; and
    (ii) a specific binding partner for a second analyte;
  (b) a first conductor in operable contact with the first end of the chromatographic medium;
  (c) a second conductor in operable contact with the second end of the chromatographic medium; and
  (d) a sample preparation zone in operable contact with a portion of the chromatographic medium between the specific binding partner for the first analyte and the specific binding partner for the second analyte; and
(2) a second opposable component including:
  (a) an absorber;
  (b) a first applicator separated from the absorber and containing a specific binding partner to the first analyte labeled with a detectable label in a form that can be resolubilized by the addition of an aqueous liquid to the first applicator; and
  (c) a second applicator separated from the absorber and containing a detection reagent for the second analyte in a form that can be resolubilized by the addition of an aqueous liquid to the second applicator;

In this version, the first and second opposable components are configured so that bringing the first and second opposable components into opposition: (1) causes the absorber to come into contact with the sample preparation zone and with the chromatographic medium so that the sample preparation zone and the chromatographic medium are brought into indirect contact; (2) causes the first applicator to come into operable contact with the first conductor; and (3) causes the second applicator to come into operable contact with the second conductor. This causes the absorber to draw fluid from the first and second applicators through the chromatographic medium toward the absorber.

A method for the detection and/or determination of at least two analytes in an aqueous sample using this assay device comprises the steps of:

(1) applying a first aqueous liquid to the second applicator of the assay device;

(2) applying a first aliquot of the sample to the first applicator;

(3) applying a second aliquot of the sample to the sample preparation zone;

(4) allowing the second aliquot of the sample applied to the sample preparation zone to migrate through at least a portion of the chromatographic medium including the specific binding partner for the second analyte;

(5) bringing the first and second opposable components into opposition to cause the absorber to come into contact with the sample preparation zone and with the chromatographic medium, the first applicator to come into contact with the first conductor, and the second applicator to come into contact with the second conductor;

(6) allowing the first aliquot of the sample and the resolubilized labeled specific binding partner to the first analyte to migrate through at least a portion of the chromatographic medium containing the immobilized specific binding partner to the first analyte and allowing the resolubilized detection reagent for the second analyte to migrate through at least a portion of the chromatographic medium containing the immobilized specific binding partner to the second analyte; and (7) detecting and/or determining the first analyte and the second analyte by observing and/or measuring the labeled specific binding partner to the first analyte bound to the zone of the immobilized specific binding partner to the first analyte and the detection reagent bound to the zone of the immobilized specific binding partner for the second analyte.

An alternative version of the second embodiment comprises:

(1) a first opposable component including:
  (a) a first chromatographic medium having a first end and a second end, the chromatographic medium having thereon in a discrete zone a specific binding partner for a first analyte;

(b) a second chromatographic medium having a first end and a second end, the second chromatographic medium having thereon in a discrete zone a specific binding partner for a second analyte;

(c) a first conductor in operable contact with the first end of the first chromatographic medium;

(d) a second conductor in operable contact with the second end of the second chromatographic medium; and (e) a sample preparation zone in operable contact with the second end of the first chromatographic medium;

(2) a second opposable component including:

(a) an absorber;

(b) a first applicator separated from the absorber and containing a specific binding partner to the first analyte labeled with a detectable label in a form that can be resolubilized by the addition of an aqueous liquid to the first applicator;

(c) a second applicator separated from the absorber and containing a detection reagent for the second analyte in a form that can be resolubilized by the addition of an aqueous liquid to the second applicator.

In this version of the second embodiment, the first and second opposable components are configured so that bringing the first and second opposable components into opposition: (1) causes the absorber to come into contact with the sample preparation zone and with the first chromatographic medium; (2) causes the first applicator to come into operable contact with the first conductor; and (3) causes the second applicator to come into contact with the second conductor so that the absorber draws fluid from the first and second applicators through the first and second chromatographic media to the absorber.

This version of the second embodiment of the device can be used in a method of detecting and/or determining at least two analytes in a test sample that is similar to that of the method of use of the first version of the second embodiment.

BRIEF DESCRIPTION OF THE DRAWINGS

These and other features, aspects, and advantages of the present invention will become better understood with reference to the following description, appended claims, and accompanying drawings where:

FIG. 1A is a depiction of an embodiment of an assay device according to the present invention in which the first opposable component has a first applicator and the second opposable component has a second applicator, shown in open position;

FIG. 1B is a sectional rear view of the device of FIG. 1A with the components in opposition;

FIG. 2A is a depiction of a first version of a second embodiment of an assay device according to the present invention with one applicator and one chromatographic medium divided into sectors, shown in open position;

FIG. 2B is a sectional rear view of the device of FIG. 2A with the components in opposition;

DESCRIPTION

Definitions

Figure 3A:
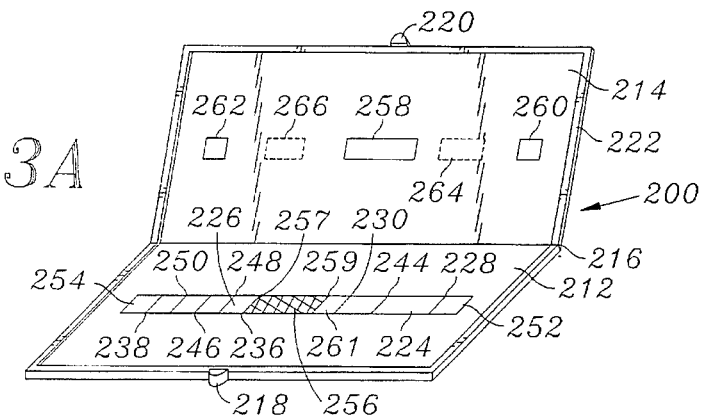
FIG. 3A is a depiction of a second version of the second embodiment of an assay device according to the present invention with one applicator bridging two chromatographic media, shown in open position.

In the context of this disclosure, the following terms are defined as follows unless otherwise indicated:

Specific Binding Partner: A member of a pair of molecules that interact by means of specific non-covalent interactions that depend on the three-dimensional structures of the molecules involved. Typical pairs of specific binding partners include antigen-antibody, hapten-antibody, hormone-receptor, nucleic acid strand-complementary nucleic acid strand, substrate-enzyme, inhibitor-enzyme, carbohydrate-lectin, biotin-avidin, and virus-cellular receptor.

Operable Contact: Two solid components are in operable contact when they are in contact, either directly or indirectly, in such a manner that an aqueous liquid can flow from one of the two components to the other substantially uninterruptedly, by capillarity or otherwise. "Direct contact" means that the two elements are in physical contact, such as edge-to-edge or front-to-back. Typically, when two components are in direct contact, they are overlapped with an overlap of about 0.5 to about 3 mm. However, the components can be placed with abutting edges. "Indirect contact" means that the two elements are not in physical contact, but are bridged by one or more conductors.

Analyte: The term "analyte" includes both the actual molecule to be assayed and analogues and derivatives thereof when such analogues and derivatives bind another molecule used in the assay in a manner substantially equivalent to that of the analyte itself.

Antibody: The term "antibody" includes both intact antibody molecules of the appropriate specificity and antibody fragments (including Fab, F(ab'), and F(ab')$_2$ fragments) as well as chemically modified intact antibody molecules and antibody fragments, including hybrid antibodies assembled by in vitro reassociation of subunits. Unless otherwise specified, the term "antibody" includes both polyclonal and monoclonal antibodies.

Secondary Specific Binding Partner: An additional specific binding partner that binds to a member of a pair of specific binding partners when the pair of specific binding partners is interacting is designated a secondary specific binding partner. However, the binding of the secondary specific binding partner to a member of the pair of specific binding partners need not occur only when the pair of specific binding partners interacts. For example, a pair of specific binding partners can comprise Giardia antigen and rabbit anti-Giardia antibody. In that case, the secondary specific binding partner can be goat anti-rabbit IgG antibody, which will bind to the rabbit anti-Giardia antibody. The binding of the goat anti-rabbit IgG antibody to the rabbit anti-Giardia antibody does not require binding of the rabbit anti-Giardia antibody to the Giardia antigen. The secondary specific binding partner can be specific for the species, class, or subclass of an antibody specific binding partner to which it binds. Alternatively, when one of the specific binding partners is labeled with biotin, the secondary specific binding partner can comprise a molecule conjugated to avidin to make use of the specificity and tight binding of the biotin-avidin link.

I. PRINCIPLES OF OPERATION OF INTERRUPTED-FLOW ASSAY DEVICES

In many cases, it is desirable to perform multiple assays in a single test strip. This can be done in testing for a number of conditions or for multiple viruses. Although this can be done on multiplex devices that have multiple chromatographic media, this is not practical when one of the assays must be performed in a bidirectional mode while another assay is performed in a unidirectional mode. This is typically the case if one of the assays is for an antigen or a hapten and the other assay is for an antibody, i.e., a serological assay. For example, it can be useful to test for an antibody to human immunodeficiency virus (HIV) and a HIV-specific antigen, such as a protein produced by the virus designated p24. Another example is testing for feline leukemia virus (FeLV) and antibody to feline immunodeficiency virus (FIV) in the same serum sample.

While assays of antigens and haptens can be carried out in either a one-directional or a two-directional format, it is strongly preferred to perform serological assays of antibodies in a two-directional format. This is because the analyte to be detected is normally detected on the basis of a specificity unrelated to the specificity that causes the antibody to bind to its corresponding antigen. The presence of other antibodies with other specificities would therefore interfere with that detection step. For example, if antibody to FIV is being assayed, and the detection reagent is a labeled rabbit antibody to cat immunoglobulins, all cat immunoglobulins present on the test strip will bind the detection reagent. This generally creates unacceptably high backgrounds leading to low sensitivity and irreproducibility.

To overcome these problems, I have developed assay devices that split flow to perform multiple assays on a single test strip. These devices operate by performing two tests on the same strip, either by providing for a flow outward from a centrally located sample preparation zone for one of the assays while applying a second sample on a separate applicator, or by interrupting the flow of the sample by an absorber as discussed below to allow for flow in the second direction.

A. Principles of Operation

Assay devices according to the present invention operate by dividing the flow in a chromatographic medium so that the two assays on separate analytes can be performed. The chromatographic medium is incorporated in an assay device that includes two or more opposable components that can be brought into opposition to apply pressure to the chromatographic medium and to other fluid-containing or fluid absorbing-elements present in the assay device. This can apply an absorber or absorbers to the chromatographic medium, or can apply an applicator or applicators to it. The absorbers and/or applicators are located on an opposable component different than the opposable component on which the chromatographic medium is located. This sequence of operation results in the flow of the reagents in a predetermined pattern to perform two assays in one test device.

In one embodiment of the present invention, a single sample is used, and during chromatography in the first direction, the components are opposed and the flow is interrupted in the first direction at a point of the chromatographic medium removed from its ends. Simultaneously, an applicator is placed in contact with the chromatographic medium to apply a detection reagent, which flows in the second direction, i.e., opposite from the direction of flow of the sample. Thus, one-directional and two-directional flow are achieved in the same chromatographic medium for assay of two analytes simultaneously.

In the second embodiment, a sample preparation zone is located between two sectors of a chromatographic medium. The separation between two sectors can either be structural or functional; i.e., the chromatographic medium can be physically continuous or it can be divided. In this embodiment, the flow outward from the sample preparation zone is used for one of the assays by applying a detection reagent to the chromatographic medium, which flows through it in a direction opposite to the flow of the sample, thus performing a bidirectional assay. The other assay is performed by adding a second sample and a labeled specific binding partner for the analyte to the chromatographic medium and allowing them to flow through the chromatographic medium in the same direction. This direction is opposite to the direction of the sample flow in the first assay.

In general, an assay device according to the present invention comprises:

(1) a first opposable component including at least one chromatographic medium having a specific binding partner to the first analyte and a specific binding partner to the second analyte immobilized thereto in separate, discrete, non-overlapping zones; and (2) a second opposable component including an absorber. The first and second opposable components are configured such that bringing the first and second opposable components into opposition causes the absorber to come into operable contact with at least one chromatographic medium so that the zone containing the specific binding partner to the first analyte is functionally divided from the zone containing the specific binding partner to the second analyte so that both analytes can be detected.

Typically, the detection of the first analyte occurs by formation of a ternary complex involving the first analyte, a labeled specific binding partner to the first analyte, and the immobilized specific binding partner to the first analyte. The detection of the second analyte occurs by formation of a ternary complex involving the second analyte, a detection reagent for the second analyte, and the immobilized specific binding partner to the second analyte.

The second opposable component can include at least one applicator. Typically, the second opposable component includes at least two applicators, an applicator containing a labeled specific binding partner for the first analyte and an applicator containing a detection reagent for the second analyte.

Typically, the first and second opposable components are configured such that when the first and second opposable components are brought into opposition, the absorber is in operable contact with the chromatographic medium. This causes the device to perform a one-dimensional chromatographic specific binding assay for the first analyte and a two-dimensional specific binding assay for the second analyte.

In general, a first embodiment of the assay device comprises:

(1) a first opposable component including:
   (a) a chromatographic medium having thereon in discrete, separated, non-overlapping zones:
      (i) a specific binding partner for a first analyte; and
      (ii) a specific binding partner for a second analyte; and
   (b) a first applicator to apply a sample and a labeled specific binding partner to the first analyte to the chromatographic medium; and (2) a second opposable component including:
  (a) a second applicator to apply a detection reagent for the second analyte to the chromatographic medium; and
  (b) an absorber, which, when the first and second opposable components are brought into opposition, is in operable contact with the chromatographic medium and functionally divides the chromatographic medium into two sectors, the first sector for the detection of the first analyte and a second sector for the detection of the second analyte.

In general, a second embodiment of the assay device comprises:

(1) a first opposable component including:
  (a) at least one chromatographic medium having thereon in discrete, separated, non-overlapping zones:
    (i) a specific binding partner for a first analyte; and
    (ii) a specific binding partner for a second analyte;
  (b) a sample preparation zone separating the specific binding partner for the first analyte and the specific binding partner for the second analyte on the at least one chromatographic medium; and (2) a second opposable component including:
  (a) an absorber;
  (b) a first applicator; and
  (c) a second applicator.

The first and second opposable components are configured such that when the first and second opposable components are brought into opposition: (1) the first applicator applies a labeled specific binding partner to the first zone of the chromatographic medium; (2) the second applicator applies a detection reagent for the second analyte to the second zone of the chromatographic medium; and (3) the absorber functionally divides the first zone from the second zone so that the labeled specific binding partner to the first analyte is substantially excluded from the second zone and the detection reagent for the second analyte is substantially excluded from the first zone.

B. Elements Common to Devices According to the Present Invention

A number of elements are common to assay devices according to the present invention and are discussed here for convenience.

1. The Chromatogaphic Medium

The chromatographic medium is a strip. Typically, the strip is substantially planar, although this is not required in all applications. It is typically rectangular, having first and second ends and first and second surfaces. Throughout this description, the term "first end" refers either to the end to which sample is first supplied to the chromatographic medium or to the end that is closer to the point at which detection of the first analyte occurs. The term "second end" applies to the opposite end of the chromatographic medium. The chromatographic medium is composed of a material or materials suitable as a medium for thin layer chromatography of analyte and analyte-antibody conjugates, such as nitrocellulose, nylon, rayon, cellulose, paper, or silica. Preferably, the chromatographic medium is nitrocellulose. The chromatographic medium can be pretreated or modified as needed. Typically, the chromatographic medium is translucent, so that colored bands appearing on it can be viewed from either side. The chromatographic medium can be composed of two or more sectors with different properties, such as thickness or porosity. For example, if the first analyte is an antigen and the second analyte is an antibody in a serological assay, it can be preferred to have one portion of the chromatographic medium be nitrocellulose with a porosity of 5 μm, for assay of the analyte, and the second sector have a porosity of 12 μm, for efficient assay of an antibody in serum. Other variations of the chromatographic medium can be used. For example, it may be possible to treat one portion of the medium but not the other with a reagent that facilitates the assay.

2. Absorbers

In a number of devices according to the present invention, an absorber is in operable contact with a portion of the chromatographic medium at some stage of the assay. The absorber can be made of any bibulous material that holds an aqueous liquid sufficiently so liquid can be drawn through the chromatographic medium and accumulated in the absorber. Typical materials include, but are not limited to, filter paper.

3. Other Fluid-Carrying Elements

As described below, in particular devices according to the present invention, other fluid-carrying elements can be employed as sample preparation zones, applicators, conjugate zones, and/or conductors. These elements are prepared of hydrophilic media that pass aqueous liquids without substantially absorbing them. Such materials are well-known in the art. In some cases, these elements can have incorporated therein a component in dry form that can be resolubilized by addition of a aqueous liquid to the element. The aqueous liquid can be either the sample migrating through the element or another separate aqueous liquid.

4. Opposable Components

Assay devices according to the present invention comprise two or more opposable components, typically two opposable components. The bodies of the opposable components are preferably made of laminated cardboard that is sufficiently impervious to moisture to contain the liquids involved in the performance of the assay carried out by the device. Other cellulose-based materials, such as paperboard or solid bleached sulfite (SBS) can also be used. Alternatively, the bodies of the opposable components can be made of plastic that is impervious to moisture. A suitable plastic is a polycarbonate plastic such as Lexan™.

Typically, the first and second opposable components are substantially planar.

The opposable components are connected so that when they are opposed, the elements on their surfaces are reproducibly brought into contact. Typically, they are joined by a hinge, preferably made of a material impermeable to aqueous liquids, such as a plastic that can be compatibly joined with or is the same as the material used for the first and second opposable components.

The device also has means for opposing the opposable components and applying pressure thereto. The pressure applied is sufficient to transfer fluid from one opposable component to another opposable component in a direction substantially normal to the opposable components so that the fluid is applied to the chromatographic medium for detection and/or determination of the analyte thereon. The pressure also drives fluid through the chromatographic medium to accelerate the process of chromatography, giving a detectable result in less time. Additionally, the pressure can make possible the performance of steps, such as extraction steps, in the device, and can be used to remove excess fluid from the chromatographic medium by absorbers to reduce the background of the assays. The pressure is generated by placing the opposable components into opposition and maintained by holding the components into opposition by engagers such as locks or clasps.

II. ASSAY DEVICES

Device With Undivided Chromatographic Medium Employing Interrupted Flow in One Direction One embodiment of the present invention is a device with a undivided chromatographic medium employing interrupted flow in one direction. In the operation of this device, bringing the first and second opposable components together causes an absorber to come into operable contact with a portion of the chromatographic medium. This reverses flow for one of the assays while allowing flow to continue in the original direction for the other assay. Thus, this device performs a unidirectional immunochromatographic assay and a bidirectional immunochromatographic assay in the same assay device. As used herein, the term "immunochromatographic" includes not only assays employing antibodies, but also assays employing other proteins with specific binding affinity for analytes, because the general principles of their operation is the same.

This embodiment of an assay device according to the present invention comprises:

(1) a first opposable component including:
  (a) a chromatographic medium having a first end, a second end, and first and second surfaces, the chromatographic medium having thereon in discrete, separated, non-overlapping zones:
    (i) a specific binding partner for a first analyte;
    (ii) a specific binding partner for a second analyte;
  (b) a conjugate zone containing a specific binding partner to the first analyte labeled with a first detectable label, the specific binding partner being present in a form that can be resolubilized by the addition of an aqueous liquid to the conjugate zone, the conjugate zone being in operable contact with the first end of the chromatographic medium;
  (c) a first applicator in operable contact with the conjugate zone, the conjugate zone bridging the first applicator and the first end of the chromatographic medium; and
  (d) a conductor in operable contact with the second end of the chromatographic medium; and (2) a second opposable component including:
  (a) an absorber; and
  (b) a second applicator separated from the absorber, the second applicator containing a detection reagent for the second analyte in a form that can be resolubilized by the addition of an aqueous liquid to the second applicator.

The first and second opposable components are configured so that bringing the first and second opposable components into opposition: (1) causes the second applicator to come into contact with the conductor; and (2) causes the absorber to come into contact with the chromatographic medium at a point between the specific binding partner for the first analyte and the specific binding partner for the second analyte. This results in the absorbers drawing fluid from the first applicator through a portion of the chromatographic medium from the first end of the chromatographic medium to the specific binding partner for the first analyte, and simultaneously drawing fluid from the second applicator through a portion of the chromatographic medium from the second end of the chromatographic medium to the specific binding partner for the second analyte.

In other words, the assay for the first analyte is unidirectional and remains unidirectional after the applicator is applied. This assay is unidirectional because the sample and the labeled specific binding partner for the first analyte move in the same direction. However, the assay for the second analyte is bidirectional because the sample moves in one direction and the detection reagent for the second analyte moves in the opposite direction. In this embodiment, the flow of sample for the assay of the second analyte is cut off when the absorber is placed in operable contact with the chromatographic medium. Typically, the second analyte is an antibody produced by a mammalian species in response to an antigen and the detection reagent for the second analyte is a labeled antibody that binds the second analyte on the basis of a specificity unrelated to the specificity by which the second analyte binds its corresponding antigen. Where the second analyte is an antibody, the specific binding partner bound to the chromatographic medium is typically an antigen or an antigen analogue for which the antibody that is the second analyte has specific binding affinity. For example, if the second analyte is antibody to feline immunodeficiency virus (FIV), the specific binding partner bound to the chromatographic medium can be the protein antigen of the FIV virus against which the antibody is directed. The detection reagent can be labeled goat anti-cat IgG. The detection reagent can also detect the antibody that is the second analyte on the basis of a specificity such as a subclass specificity. For example, if it is desired to detect an antibody that is a human IgG1 immunoglobulin, the detection reagent can be a labeled goat anti-human IgG1 antibody produced by immunizing the goat with a purified human IgG1 immunoglobulin and then absorbing out determinants common to other subclasses. Such techniques are well known in the art of immunochemistry and need not be described further here.

Typically, when the second analyte is an antibody, the first analyte is an antigen.

The chromatographic medium can comprise two sectors of different porosities when the first analyte is an antigen and the second analyte is an antibody. The first sector includes the specific binding partner for the first analyte and has a porosity suitable for the detection of the first analyte as an antigen. The second sector includes the specific binding partner for the second analyte and has a porosity suitable for the detection of the analyte as an antibody in a serological sample. Typically, the diameter of the pores in the second sector is greater than the diameter of the pores in the first sector. For example, for the detection of FeLV and antibody to FIV, the first sector can be nitrocellulose with a porosity of 5 μm and the second sector can be nitrocellulose with a porosity of 12 μm.

This device is depicted in FIGS. 1A and 1B. FIG. 1A shows the device in its open position, while FIG. 1B is a sectional rear view of the device, showing details of the components in opposition.

The device 10 has first and second opposable components 12 and 14, joined by a hinge 16. The first and second opposable components 12 and 14 have engagers such as locks 18 and 20 that hold the opposable components together. The first and second opposable components 12 and 14 also have a ridge or gasket 22 surrounding them to prevent the escape of samples or reagents. The first opposable component 12 includes a chromatographic medium 24 with first and second ends 26 and 28 and first and second surfaces 30 and 32. The chromatographic medium 24 has thereon in discrete, separated, non-overlapping zones, a specific binding partner for the first analyte 34 and a specific binding partner for the second analyte 36. Preferably, the chromatographic medium 24 also has thereon an area of a resolubilizable dye 38, and a control zone 40 that binds the detection reagent for the second analyte. Marked on or immediately adjacent to the chromatographic medium 24 is a limit line 42.

The first opposable component 12 also includes a conjugate zone 44 that contains a specific binding partner for the first analyte labeled with a detectable label in resolubilizable form. The first opposable component 12 also includes a first applicator 46 for application of the sample. The first applicator 46 is in operable contact with the conjugate zone 44, so that the conjugate zone 44 bridges the first applicator 46 and the first end 26 of the chromatographic medium 24. The first opposable component 12 also includes a conductor 48 in operable contact with the second end 28 of the chromatographic medium 24.

The second opposable component 14 includes an absorber 50 and a second applicator 52 separated from the absorber 50. The second applicator 52 contains a detection reagent for the second analyte in a form that can be resolubilized by the addition of an aqueous liquid to the second applicator 52. Preferably, the second opposable component 14 also includes a first window 54 and a second window 56. The first window 54 allows viewing of the specific binding partner for the first analyte 34 when the first and second opposable components 12 and 14 are brought into opposition. The second window 56 allows viewing of the specific binding partner for the second analyte 36 when the first and second opposable components 12 and 14 are brought into opposition.

Bringing the first and second opposable components 12 and 14 into opposition causes the second applicator 52 to come into contact with the conductor 48 and causes the absorber 50 to come into contact with the first surface 30 of the chromatographic medium 24 at a point between the specific binding partner for the first analyte 34 and the specific binding partner for the second analyte 36. This causes the absorber 50 to draw fluid from the first applicator 46 through a portion of the chromatographic medium 24 from the first end 26 of the chromatographic medium 24 to the specific binding partner for the first analyte 34, and simultaneously draws fluid from the second applicator 52 through a portion of the chromatographic medium 24 from the second end 28 of the chromatographic medium 24 to the specific binding partner for the second analyte 36.

In use, a sample is applied to the first applicator 46 and allowed to migrate from the first applicator 46 through the conjugate zone 44 and then through at least a portion of the chromatographic medium 24 including the specific binding partner for the first analyte 36. Preferably, the sample moves through the area of the resolubilizable dye 36 and the control zone 40. An aqueous liquid is added to resolubilize the detection reagent in the second applicator 52. When the resolubilized dye and the sample reach the limit line 42, the first and second opposable components 12 and 14 are brought into opposition to apply the second applicator 52 to the conductor 48 and to apply the absorber 50 to the first surface 30 of the chromatographic medium 24. This reverses the flow for the second assay so that the detection reagent for the second analyte is drawn back across the chromatographic medium 24 in the opposite direction to the direction that the sample migrated through the chromatographic medium 24. This performs a bidirectional immunochromatographic assay for the second analyte. At the same time, migration can continue from the sample in the first applicator through the conjugate zone 44 to the absorber 50 in operable contact with the chromatographic medium 24. This accomplishes a unidirectional immunochromatographic assay for the first analyte.

Typically, the chromatographic medium has dimensions of about 0.5 inch to about 1 inch for its length and of about 0.125 inch to about 0.375 inch for its width.

Typically, the sample volume is from about 25 to about 250 µl, more typically about 100 µl. Typically, to achieve results, the time from the application of the sample until the sample reaches the limit line is about 0 to 60 seconds. The total time for performance of the assay is typically about 1 to 2 minutes. Typically, the assay is performed at room temperature, although it can be performed at 4° C. or up to 37° C. or higher in some cases, depending upon the nature of the analyte, the chromatographic medium, and the specific binding partners. In some cases, performing the assay at a lower temperature may be desirable to limit degradation of the sample or of a specific binding partner, while in other cases, performing the assay at a higher temperature with suitable analytes and specific binding partners may speed up the assay.

B. Devices with Chromatographic Medium Divided into Sectors

In another embodiment of the present invention a sample preparation zone is located between two sectors of the chromatographic medium, either with a continuous or a divided chromatographic medium. In this embodiment, as described above, the sample flowing from the sample preparation zone is used to perform a bidirectional immunochromatographic assay, typically a serological assay. A separate aliquot of the sample is applied to the chromatographic medium for the performance of a unidirectional immunochromatographic assay.

1. Device with Sample Preparation Zone in Operable Contact with Chromatographic Medium One version of this embodiment has a sample preparation zone in operable contact with the chromatographic medium. In this device, the chromatographic medium is continuous in structure, although it is divided functionally because flow occurs from one end of the sample preparation zone outward toward one end of the chromatographic medium. The other end of the sample preparation zone is not in operable contact with the chromatographic medium until the first and second opposable components are brought into opposition and an absorber is brought into operable contact with the sample preparation zone and chromatographic medium to withdraw fluid from them. This device comprises:

(1) a first opposable component including:
 (a) a chromatographic medium having a first end and a second end, the chromatographic medium having thereon in discrete, separated, non-overlapping zones:
  (i) a specific binding partner for a first analyte; and
  (ii) a specific binding partner for a second analyte;
 (b) a first conductor in operable conduct with the first end of the chromatographic medium;
 (c) a second conductor in operable contact with the second end of the chromatographic medium; and
 (d) a sample preparation zone in operable contact with a portion of the chromatographic medium between the specific binding partner for the first analyte and the specific binding partner for the second analyte; and (2) a second opposable component including:
 (a) an absorber;
 (b) a first applicator separated from the absorber and containing a specific binding partner to the first analyte labeled with a detectable label in a form that can be resolubilized by the addition of an aqueous liquid to the first applicator; and
 (c) a second applicator separated from the absorber and containing a detection reagent for the second analyte in resolubilizable form.

In this device, the first and second opposable component are configured so that bringing the first and second opposable components into opposition: (1) causes the absorber to come into contact with the sample preparation zone and with the chromatographic medium so that the sample preparation zone and the chromatographic medium are brought into indirect contact; (2) causes the first applicator to come into operable contact with the first conductor; and (3) causes the second applicator to come into operable contact with the second conductor. Thus, the absorber draws fluid from the first and second applicators through the chromatographic medium toward the absorber. This performs a unidirectional assay for the first analyte while performing a bidirectional assay for the second analyte, because the flow from the second applicator through the chromatographic medium is in the direction opposite to the flow of the sample from the sample preparation zone.

The chromatographic medium, as described above, can be divided into two or more sectors of different porosities to accommodate the particular analytes being assayed. In particular, the first sector can include the specific binding partner for the first analyte, and have a porosity suitable for the detection of the first analyte as an antigen. The second sector can include the specific binding partner for the second analyte and can have a porosity suitable for the detection of the second analyte as an antibody in a serological sample.

This device is depicted in FIGS. 2A and 2B. FIG. 2A depicts the device in the open position, while FIG. 2B is a sectional rear view of the device showing the components in opposition. The device 100 has first and second opposable components 112 and 114 joined by a hinge 116. The first and second opposable components 112 and 114 have engagers such as locks 118 and 120, to hold the opposable components together. The first and second opposable components 112 and 114 also have a ridge or gasket 122 surrounding them to prevent leakage.

The first opposable component 112 includes a chromatographic medium 124 with first and second ends 126 and 128 and first and second surfaces 130 and 132. The chromatographic medium 124 has therein in discrete, separated, non-overlapping zones, a specific binding partner for the first analyte 134 and a specific binding partner for the second analyte 136. The chromatographic medium 124 also preferably includes a control zone 138 to bind the detection reagent for the second analyte. Marked on or immediately adjacent to the chromatographic medium 124 is a limit line 140.

The first opposable component 112 also has a first conductor 142 in operable contact with the first end 126 of the chromatographic medium 124 and a second conductor 144 in operable contact with the second end 128 of the chromatographic medium 124.

The first opposable component 112 also includes a sample preparation zone 146 with a first end 147 and a second end 149. The first end 147 of the sample preparation zone 146 is in operable contact with a portion 133 of the chromatographic medium 124 between the specific binding partner for the first analyte 134 and the specific binding partner for the second analyte 136. The portion 133 lies closer to the specific binding partner for the second analyte 136. The sample preparation zone 146 is placed adjacent to the first surface 130 of the chromatographic medium 124 but is preferably insulated therefrom so that fluid flow does not occur from the sample preparation zone 146 to the first surface 130 of the chromatographic medium 124. Also, fluid flow preferably does not occur from the second end 149 of the sample preparation zone 146 to the chromatographic medium 124 until the first and second opposable components 112 and 114 are brought into opposition, with a gap 151 existing between the second end 149 of the sample preparation zone 146 and the chromatographic medium 124. The sample preparation zone 146 preferably contains a resolubilizable dye to indicate the progress of the sample through the chromatographic medium 124. The sample preparation zone 146 can also contain one or more reagents for treatment of the sample.

The second opposable component 112 includes an absorber 148, a first applicator 150 separated from the absorber 148 and containing a specific binding partner for the first analyte labeled with a detectable label in resolubilizable form, and a second applicator 152 separated from the absorber 148 and containing a detection reagent for the second analyte in resolubilizable form. The second opposable component 112 further preferably includes a first aperture 154 and a second aperture 156 for viewing of the specific binding partner for the first analyte 134 and the specific binding partner for the second analyte 136, respectively, when the first and second opposable components 112 and 114 are brought into opposition to close the device 100.

When the first and second opposable components 112 and 114 are brought into opposition, the absorber 148 comes into operable contact with the sample preparation zone 146, including its second end 149, and with a portion 157 of the chromatographic medium 124 located closest to the second end 149 of the sample preparation zone 146 to withdraw fluid from the sample preparation zone 146 and the chromatographic medium 124. The first applicator 150 comes into operable contact with the first conductor 142, and the second applicator 152 comes into operable contact with the second conductor 144.

In use, a first aqueous liquid is applied to the second applicator 152, and a first aliquot of the sample to be assayed is applied to the first applicator 150. A second aliquot of the sample is applied to the sample preparation zone 146. The second aliquot of the sample applied to the sample preparation zone 146 is allowed to migrate from the first end 147 of the sample preparation zone 146 through at least the portion 133 of the chromatographic medium 124 and through the specific binding partner for the second analyte 136. The first and second opposable components 112 and 114 are then brought into opposition to cause the absorber 148 to come into contact with the sample preparation zone 146, including its second end 149, and with the portion 157 of the chromatographic medium 124. This also causes the first applicator 150 to come into contact with the first conductor 142, and the second applicator 152 to come into contact with the second conductor 144. The resolubilized labeled specific binding partner for the first analyte as well as the first aliquot of the sample, originally applied to the first applicator 150, are then allowed to migrate through at least the region of the chromatographic medium containing the immobilized specific binding partner to the first analyte 134. If the first analyte is present in the sample, a ternary complex including the first analyte, the immobilized specific binding partner to the first analyte, and the resolubilized labeled specific binding partner for the first analyte is formed at zone 134. This complex is a typical sandwich complex.

The resolubilized detection reagent for the second analyte is then allowed to migrate through at least a portion of the chromatographic medium 136 containing the immobilized specific binding partner to the second analyte. This flow is driven by the absorber 148 withdrawing fluid from the sample preparation zone 146 in order to reverse flow for the bidirectional serological assay performed for the second analyte. If the second analyte is present in the sample, a ternary complex involving the immobilized specific binding partner to the second analyte, the second analyte, and the detection reagent is formed at zone 136. The first analyte and the second analyte are then detected by observing and/or measuring the labeled specific binding partner to the first analyte bound at zone 134 and the detection reagent for the second analyte bound at zone 136.

Typically, the first and second opposable components 112 and 114 are closed when the sample migrating from the sample preparation zone 146 reaches the limit line 140. This point is determined by observing the migration of the visible dye in the sample preparation zone 146 after it is resolubilized by the sample.

Typically, the migration proceeds for about 30 seconds to 2 minutes before the first and opposable components 112 and 114 are closed. The results are read after an additional development time that varies with the sample, the dimensions of the chromatographic medium, and the nature of the analytes and the specific binding partners, but which is typically from about 30 second to about 2 minutes.

2. Device with Sample Preparation Zone Interrupting Chromatographic Medium

The device described above can be varied by having the sample preparation zone interrupt the chromatographic medium instead of being placed in insulated contact with its first surface, so that there are two separated chromatographic media. In this device, flow is outward from the sample preparation zone to only the second chromatographic medium when the first and second opposable components are not in opposition. The sample preparation zone and the first chromatographic medium are bridged by the absorber when the first and second opposable components are in contact.

The second component of this version of the device is basically similar to that of the device described above.

The device comprises:

(1) a first opposable component including:
  (a) a first chromatographic medium having a first end and a second end, the chromatographic medium having thereon in a discrete zone a specific binding partner for a first analyte;
  (b) a second chromatographic medium having a first end and a second end, the second chromatographic medium having thereon in a discrete zone a specific binding partner for a second analyte;
  (c) a first conductor in operable contact with the first end of the first chromatographic medium;
  (d) a second conductor in operable contact with the second end of the second chromatographic medium; and
  (e) a sample preparation zone in operable contact with the first end of the second chromatographic medium;

(2) a second opposable component including:
  (a) an absorber;
  (b) a first applicator separated from the absorber and containing a specific binding partner to the first analyte labeled with a detectable label in a form that can be resolubilized by the addition of an aqueous liquid to the first applicator; and
  (c) a second applicator separated from the absorber and containing a detection reagent for the second analyte in resolubilizable form.

The first and second opposable components are configured so that bringing the first and second opposable components into opposition: (1) causes the absorber to come into contact with the sample preparation zone and with the first chromatographic medium; (2) causes the first applicator to come into operable contact with the first conductor; and (3) causes the second applicator to come into contact with the second conductor. This causes the absorber to draw fluid from the first and second applicators through the first and second chromatographic media to the absorber, so that a unidirectional assay is performed for the first analyte and a bidirectional assay is performed for the second analyte.

Figure 3B:
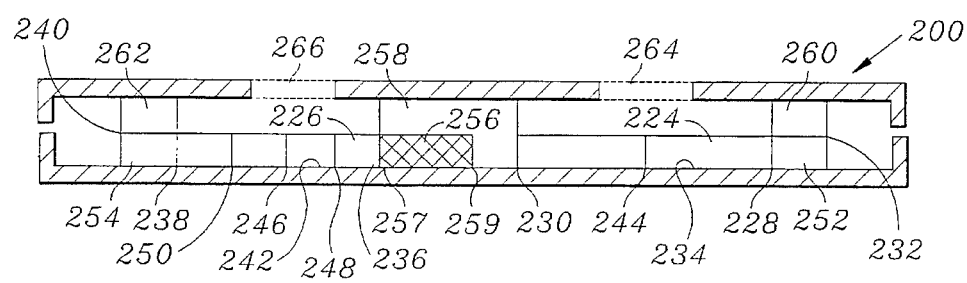
FIG. 3B is a sectional rear view of the device of FIG. 3A with the components in opposition.

This device is depicted in FIGS. 3A and 3B. FIG. 3A shows the device in the open position, while FIG. 3B is a sectional rear view of the device with the components in opposition. The device 200 has first and second opposable components 212 and 214 joined by a hinge 216, with engagers 218 and 220. The first and second opposable components 212 and 214 have a ridge or gasket 222 surrounding them to prevent leakage of samples or reagents. The first opposable component 212 includes first and second chromatographic media 224 and 226. The first chromatographic medium 224 has first and second ends 228 and 230 and first and second surfaces 232 and 234. The second chromatographic medium 226 has first and second ends 236 and 238 and first and second surfaces 240 and 242. The first chromatographic medium 224 has in a discrete zone a specific binding partner for the first analyte 244. The second chromatographic medium 226 has in a similar discrete zone a specific binding partner for the second analyte 246, and preferably, a control zone 248 that binds the detection reagent for the second analyte. Marked on or immediately adjacent to the second chromatographic medium 226 is a limit line 250. The first opposable component 212 also has a first conductor 252 in operable contact with the first end 228 of the first chromatographic medium 224, and a second conductor 254 in operable contact with the second end 238 of the second chromatographic medium 226. The first opposable component 212 also has a sample preparation zone 256 with first and second ends 257 and 259. The first end 257 of the sample preparation zone 256 is in operable contact with the first end 236 of the second chromatographic medium 226. The second end 259 of the sample preparation zone 256 is not in operable contact with the second end 230 of the first chromatographic medium 224 until the first and second opposable components 212 and 214 are brought into opposition, with a gap 261 existing as described above. Typically, the sample preparation zone 256 is centrally located within the first opposable component 212. However, this is not necessary, and in some applications, an asymmetrical location of the sample preparation zone 256 may be desirable, depending on the dimensions of the chromatographic media. The sample preparation zone 256 typically contains a visible dye that can be resolubilized by the application of a sample to the sample preparation zone 256. This dye enables the user to monitor the progress of the migration of the sample through the second chromatographic medium 226.

The second opposable component 214 includes an absorber 258, a first applicator 260 separated from the absorber 258 and containing a specific binding partner for the first analyte labeled with a detectable label in resolubilizable form, and a second applicator 262, separated from the absorber 258 and containing a detection reagent for the second analyte in resolubilizable form. The second opposable component 214 also includes a first aperture 264 to allow viewing of the zone of the specific binding partner to the first analyte 244 and a second aperture 266 to allow viewing of the zone of the immobilized specific binding partner for the second analyte 246 and, if present, the control zone 248.

When the first and second opposable components 212 and 214 are brought into opposition, the absorber 258 is brought into contact with the sample preparation zone 246 and with the second end 230 of the first chromatographic medium 224. The first applicator 260 is brought into contact with the first conductor 252. The second applicator 262 is brought into contact with the second conductor 254.

An assay using this embodiment is performed in essentially the same manner as that of the embodiment incorporating a single chromatographic medium with a sample preparation zone in operable contact with its first surface. Briefly, a first aqueous liquid is applied to the second applicator 262, a first aliquot of the sample is applied to the first applicator 260, and a second aliquot of the sample is applied to the sample preparation zone 246. The sample is allowed to migrate through at least a portion of the second chromatographic medium including the discrete zone of the specific binding partner to the second analyte 246 and the control zone 248, if present. When the sample reaches the limit line 250, the first and second opposable components 212 and 214 are brought into opposition, applying the labeled specific binding partner to the first analyte as well as the first aliquot of the sample in the first applicator 260 and the detection reagent for the second analyte in the second applicator 262 to the first and second conductors 252 and 254. The first aliquot of the sample and the labeled specific binding partner for the first analyte and the detection reagent for the second analyte are then allowed to migrate through the first and second chromatographic media 224 and 226 and the analytes are detected as described above. This results in a unidirectional assay being performed for the first analyte and a bidirectional assay being performed for the second analyte.

III. ANALYTES, SPECIFIC BINDING PARTNERS, AND LABELS

A. Analytes

The analytes suitable for detection with an assay device according to the present invention include antigens, haptens and antibodies. Antigens detectable with the device include hemoglobin, Streptococcus A and B antigens, antigens specific to the protozoan parasite Giardia and viral antigens, including antigens specific for viruses such as feline leukemia virus (FeLV) and the Australia antigen specific for hepatitis. In general, any protein, carbohydrate, glycoprotein, or mucoprotein that is sufficiently large to be immunogenic can be assayed as an antigen. Preparation of antibodies to such antigens is well understood in the art and is described, example in B. Harlow and D. Lane, "Antibodies: A Laboratory Manual" (Cold Spring Harbor Laboratory, Cold Spring Harbor, N.Y., 1988), pp. 53–137, incorporated herein by this reference. A particularly useful antigen with assay devices according to the present invention is FeLV antigen.

In general, haptens are assayable by procedures using assay devices according to the present invention when the hapten is sufficiently large to accommodate more than one epitope. It is recognized that not all haptens are large enough to accommodate more than one epitope; however, some haptens, though not large enough to induce antigen formation when injected by themselves, are nevertheless large enough that they possess more than one epitope. Such haptens of sufficient size are assayable with assay devices according to the present invention.

Antibodies that can be assayed include virtually all antibodies produced in mammals, including IgG, IgM, and other classes of antibodies. One antibody for which assay devices according to the present invention are particularly useful is antibody to feline immunodeficiency virus (FIV).

B. Specific Binding Partners

Specific binding partners for the analyte can include antibodies and specific binding proteins. Antibodies can include IgG, IgM, and other classes of antibodies. The antibodies can be polyclonal or monoclonal. For some applications, particularly those where a certain degree of genetic variability may exist in the analyte being screened, due to the existence of polymorphisms, polyclonal antibodies may prove most useful, because they are typically raised against a number of determinants. In situations in which a great degree of discrimination is sought between the analyte to be assayed and potentially similar and interfering analytes, and genetic variability is not a problem, monoclonal antibodies may be preferred. The use of bivalent or univalent antibody fragments, including Fab, F(ab') and F(ab')$_2$ fragments, may be desirable in some applications. Because there is no need to form a lattice of multiple interactions, the use of such fragments can reduce the background while not significantly lowering sensitivity. Also within the scope of the invention is the use of chemically modified intact antibody molecules and antibody fragments, including hybrid antibodies assembled by in vitro reassociation of subunits.

When the analyte is an antigen, the first and second specific binding partners are typically identical, but need not be. The first specific binding partner is immobilized to the chromatographic medium at the detection zone. Typically, the antibody is bound to the detection zone covalently. Methods for covalently binding antibodies to solid phases are well known in the art and are described, for example, in P. Tijssen, "Practice and Theory of Enzyme Immunoassays," (Elsevier, Amsterdam, 1985), pp. 297–328, incorporated herein by this reference. Noncovalent attachment of the antibody to the solid phase can also be used in some cases, particularly where the chromatographic medium is nitrocellulose or plastic.

Specific binding partners also include specific binding proteins, such as receptors for protein hormones. These can substitute for antibodies in the assay. They can be coupled to the chromatographic medium either covalently or noncovalently in much the same way as antibodies.

When one of the analytes to be assayed is an antibody, the first specific binding partner immobilized on the chromatographic medium is typically an antigen or an antigen analogue for which the antibody to be assayed has specific binding affinity. In some cases, the antigen analogue bound to the chromatographic medium can be extended by a spacer to limit the steric hindrance resulting from the attachment of the antigen or antigen analogue to the solid support, thereby improving binding affinity and efficiency. The spacer typically contains groups such as saturated hydrocarbon, amide, or ester linkages, although other stable spacer-forming groups are possible. Where the analyte is an antibody and the corresponding antigen is a protein, methods of attachment to the solid support similar to those above can be used. Such methods also are available for antigens or antigen analytes other than proteins. For example, cellulose can be activated with 1-(3-nitrobenzyloxymethyl) pyridinium chloride, to produce successively nitrobenzyloxymethyl, aminobenzyloxymethyl, and diazobenzyloxymethyl groups. The latter can react with several groups found in proteins, nucleic acids, and other molecules, including phenol groups and aromatic amines.

When one of the analytes to be assayed is an antibody, the detection reagent is typically a second antibody that binds the first antibody on the basis of a specificity other than the specificity by which the first antibody (i.e. the analyte) binds its corresponding antigen or hapten. For example, if the analyte is feline antibody to feline immunodeficiency virus (FIV), the first specific binding partner bound by the solid support is typically a protein from FIV that is the immunogen or the intact virus, and the detection reagent is typically anti-cat IgG antibody produced in another species by immunization of that species with cat IgG immunoglobulin.

The detection reagent can also be an antibody that is prepared on the basis of specificity other than species specificity, such as subclass specificity.

C. Labels

The second specific binding partner for the first analyte and the detection reagent for the second analyte are each labeled with a detectable label. A number of detectable labels can be used. Preferably, the detectable label is a visually detectable label, which permits detection and/or determination of the analytes by visual observation. A preferred visually detectable label is a colloidal metal label. Preferably the colloidal metal label is gold, silver, bronze, or tin; most preferably it is gold. The preparation of gold-labeled antibodies is described in J. DeMey, "The Preparation and Use of Gold Probes," in *Immunocytochemistry: Modern Methods and Applications* (J. M. Polak & S. Van-Noorden, eds., Wright, Bristol, England, 1986), ch. 8, pp. 115–145, incorporated herein by this reference. Antibodies labeled with colloidal gold are commercially available, such as from Sigma Chemical Company, St. Louis, Mo.

Alternatively, other colloidal labels, such as a colloidal sulfur label or a dye-silica label, can also be used. In a less preferred alternative, the visually detectable label can be a colored latex label. It is also possible to use other labels, such as radioactive labels, fluorescent labels, or enzyme labels.

The invention is illustrated by the following Example. The Example is for illustrative purposes only and is not to be construed as limiting the scope of the invention in any manner.

EXAMPLE

Interrupted-Flow Assay Device for Detection of Rubella and Human Chorionic Gonadotropin An interrupted-flow assay device according to the present invention was constructed to detect both rubella and human chorionic gonadotropin (hCG) in a single test. The assay for rubella is a serological assay for anti-rubella antibody, and the immunological assay for hCG.

Figure 4:
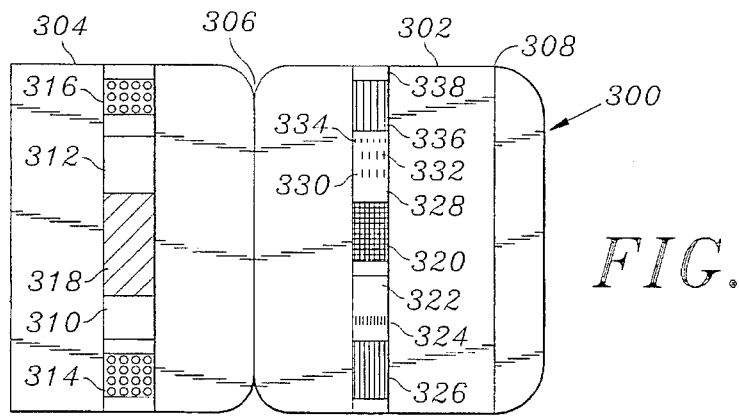
FIG. 4 is a depiction of an assay device constructed according to the present invention for the detection of anti-rubella antibody and human chorionic gonadotropin, shown in open form.
Figure 5:
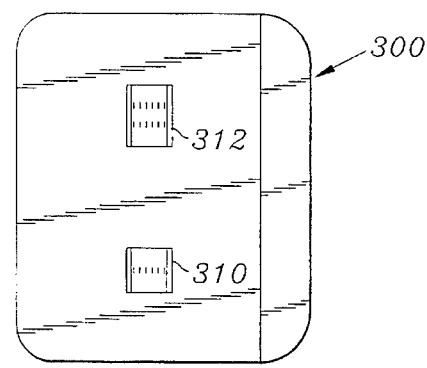
FIG. 5 is a depiction of the assay device of FIG. 4 after closing of the opposable components, showing the lines indicating the presence of the analytes through the windows of the device.

The device used for this assay is shown in FIGS. 4 and 5. FIG. 4 shows the open device 300. This device, when closed, is essentially similar to that shown in FIG. 3B. The device 300 has a first opposable component 302 and a second opposable component 304. The first and second opposable components 302 and 304 are joined by a hinge 306. The first and second opposable components 302 and 304 can be held in opposition by a bevel closure 308.

The second opposable component 304 includes a first window 310 to allow observation of the rubella test and a second window 312 to allow observation of the hCG test.

The second opposable component 304 has a first reagent pad 314 consisting of Lipore (Grade 9254 glass fiber filter, Lydall Technical Papers, Rochester, N.H.) glass fiber impregnated with a dried conjugate of anti-hCG-gold. For each pad, 10 µl of anti-hCG monoclonal antibody (Oy Medix Biochemica AB, Kauniainen, Finland) conjugated to 40 nm colloidal gold (BioCell, Cardiff, Wales, United Kingdom) was mixed with 10 µl of conjugate diluent (5 mM borate, 0.1% Triton® X-100 (octylphenoxy polyethoxyethanol), 1% bovine serum albumin, 5% sucrose, pH 8.0) and was dried at 37° C. for 30 minutes.

A second reagent pad 316 was constructed of Lipore glass fiber impregnated with dried conjugates of goat anti-human IgG-gold and goat IgG-gold. For each pad, 8.125 µl goat anti-human IgG (Jackson Laboratories, Bar Harbor, Me.) conjugated to 15 nM colloidal gold (EY Laboratories, San Mateo) was mixed with 2.0 µl goat IgG linked to 40 nm colloidal gold (BioCell) and 37.5 µl of conjugate diluent as above, and dried at 37° C. for 30 minutes.

The second opposable component 304 further includes an absorber 318 (Ahlstrom 270, Ahlstrom Filtration, Holly Springs, Pa.).

The first opposable component 302 includes a specimen pad 320 of Ahlstrom Cytosep.

The first opposable component 302 further includes a first chromatographic medium 322 of 5 µm nitrocellulose from Schleicher & Schuell (Keene, N.H.).

The first chromatographic medium 322 contains thereon a detection zone 324 of anti-hCG antibody (Binax, Portland, Me., polyclonal anti-whole hCG, 2 mg/ml). At the end of the first chromatographic medium 302 furthest from the specimen pad 320 is a first conductor 326 (Ahlstrom 1281).

The first opposable component 302 further includes a second chromatographic medium 328 comprising 12 µm nitrocellulose (Schleicher & Schuell). The second chromatographic medium 328 has thereon a control zone 330 (anti-goat IgG (O.E.M. Concepts, Toms River, N.J., 1 mg/ml ).

The second chromatographic medium 328 on the first opposable component 302 further includes a detection zone 332 containing rubella viral antigen at 0.25 mg/ml.

The first opposable component 302 further includes a printed limit line 334 and a second conductor (Ahlstrom 1281) 336. The limit line 334 is located between the detection zone 332 and the second conductor 336. The first and second chromatographic medium 322 and 328 and the first and second conductors 326 and 336 are backed by a polycarbonate test strip backing (Lexan) 338.

For operation of the test, one drop of reconstituting buffer (0.005M phosphate buffered saline, 0.4% TWEEN® 20 (polysorbate 20) , 1.25 mM HEPES, 0.0025%) Triton® X-100 (octylphenoxy polyethoxyethanol), 0.0015% EDTA, 0.025% sodium azide, pH 7.5), was added to the rubella reagent pad 316. One drop of serum from the test subject was then added to the reagent pad for the hCG 314 and the specimen pad 320. The serum in the reagent pad for hCG 314 reconstituted the anti-hCG-gold conjugate dried in the pad. The serum added to the specimen pad 320 was allowed to migrate through the second chromatographic medium 328 where, if present in the serum, anti-rubella antibody was captured by the rubella antigen immobilized at the detection zone 332.

As the serum front reached the limit line 334, the device was closed. Simultaneously, the absorber 318 made contact with the upper portion of the first chromatographic medium 322 (for determining hCG) and the lower portion of the second chromatographic medium 328 (for testing for anti-rubella antibody), as well as the specimen pad 320. The rubella reagent pad 316 applied conjugate (anti-human IgG and goat IgG) to the second conductor 336. These reagents migrated down the second chromatographic medium 328 as serum was withdrawn from the second chromatographic medium 328 by the absorber 318. Anti-rubella IgG antibody captured by rubella antigen in the detection zone 332 was labeled by the passing anti-IgG gold conjugate to give a visible line at the detection zone 332. The control line developed in the control zone 330 as the goat-IgG-gold conjugate passed the anti-goat IgG line in the control zone 330 uncaptured reagents were absorbed by the absorber 318.

The hCG reagent pad 314, to which sample had been applied, applied the conjugate and the sample to the first conductor 326, and thereby to the first chromatographic medium 322. If hCG was present in the sample, it was already labeled by gold, and as it migrated past the detection zone 324 containing anti-hCG antibody, it was captured to form a visible line at the detection zone 324 for hCG. Uncaptured reagents were absorbed by the absorber 318.

Using this device, serum have been tested to detect levels of hCG that are clinically significant. Levels of hCG greater than 25 mIU/ml and levels of rubella antibody greater than ⅛ HAI Titer were detectable using this device.

ADVANTAGES OF THE INVENTION

Chromatographic assay devices according to the present invention can perform simultaneous detection and/or determination of two analytes in the same sample using just one test in one device. The devices allow for the detection of both an antigen, by a sandwich immunoassay, and an antibody, by a serological immunoassay, in one test. This can provide for the diagnosis of two diseases or conditions at once, or, alternatively, for the detection of both an antigen associated with a pathogen or infectious agent and an antibody associated with an immune response to the pathogen or infectious agent.

Chromatographic assay devices according to the present invention also provide an advantage in being constructed of opposable elements. The use of opposable elements provides great versatility, as it permits the performance of reactions in a number of different sequences. This is possible because the use of such opposable elements allows the delivery of reagents to precisely defined regions of a test strip or other reaction component. The use of opposable elements also provides optimum performance with minimum consumption of reagents by ensuring that reagents are not wasted by being sequestered in dead volumes of apparatus. Finally, the use of opposable components provides optimum containment of possibly contaminated blood samples, each as those containing HIV or hepatitis virus.

Additionally, chromatographic assay devices according to the present invention allow the rapid and accurate detection of clinically important analytes. The construction of the devices allows more even application of the samples to the chromatographic medium, and reduces interference that might otherwise be introduced by particulates or colored samples. The use of colloidal metal labels in a resolubilizable form provides extremely rapid kinetics of labeling and improves the performance of the assay. Additionally, the construction and arrangement of the housing of the device aids in the performance of the assay by assuring the withdrawal of excess immunoglobulin-containing sample that could otherwise create interference in the serological assay.

Test methods using devices according to the present invention have a wide dynamic range and are substantially free from false negatives that may occur in other test methods at high concentrations of analyte.

Although the present invention has been described with considerable detail, with reference to certain preferred versions thereof, other versions and embodiments are possible. These versions include other arrangements of two-component devices that operate by the basic principles described herein and simultaneously perform two assays for different analytes in one assay device by blocking or restricting the flow of sample from one portion of the chromatographic medium. Therefore, the scope of the invention is determined by the following claims.

I claim:

1. An assay device for detecting at least two analytes in an aqueous sample, a first analyte that is an antigen and a second analyte that is an antibody, the assay device comprising:

(a) a first opposable component comprising at least one chromatographic medium having (1) a first end comprising a conjugate zone impregnated with a labeled specific binding partner to the first analyte, (2) an intermediate first zone comprising an immobilized specific binding partner to the first analyte, and (3) a second end having a second zone comprising an immobilized antigen which specifically binds to the second analyte;

(b) a second opposable component having an absorber which is brought into fluid communication with an area of the at least one chromatographic medium between the first and second zones thereof when the first and second opposable components are brought into physical contact; and (c) a labeled specific binding partner to the second analyte impregnated in either the first or the second opposable component in a zone in downstream fluid communication with the second zone;

wherein the first and second opposable components are capable of being brought into physical contact to provide a unidirectional chromatographic specific binding assay for the first analyte and a bidirectional chromatographic specific binding assay for the second analyte by physically contacting the absorber to the first opposable component after migration of an applied aqueous sample from the first end to the second end of the first opposable component in order to reverse fluid flow direction between the first and second ends, and detecting the first and second analytes by detecting formation of labeled ternary complexes in the first and second zones, respectively.

2. An assay device for detecting at least two analytes in an aqueous sample, a first analyte that is an antigen and a second analyte that is an antibody, the assay device comprising:

(a) a first opposable component comprising at least one chromatographic medium having (1) a first end, (2) an intermediate first zone comprising an immobilized specific binding partner to the first analyte, and (3) a second end having a second zone comprising an immobilized antigen which specifically binds to the second analyte;

(b) a second opposable component having (1) a first applicator impregnated with a labeled specific binding partner for the first analyte which is brought into fluid communication with the first zone when the first and second opposable components are brought into physical contact, (2) an absorber which is brought into fluid communication with an area of the at least one chromatographic medium between the first and second zones thereof when the first and second opposable components are brought into physical contact; and (3) a second applicator impregnated with a labeled specific binding partner for the second analyte which is brought into fluid communication with the second zone, when the first and second opposable components are brought into physical contact;

wherein the first and second opposable components are capable of being brought into physical contact to provide a unidirectional chromatographic specific binding assay for the first analyte and a bidirectional chromatographic specific binding assay for the second analyte by physically contacting the absorber to the first opposable component after migration of an applied aqueous sample from the first end to the second end of the first opposable component in order to reverse fluid flow direction between the first and second ends, and detecting the first and second analytes by detecting formation of labeled ternary complexes in the first and second zones, respectively.

3. An assay device for detecting at least two analytes in an aqueous sample, a first analyte that is an antigen and a second analyte that is an antibody, the assay device comprising:

(a) a first opposable component comprising at least one chromatographic medium having (1) a first end comprising a first applicator impregnated with a labeled specific binding partner to the first analyte, (2) an intermediate first zone comprising an immobilized specific binding partner to the first analyte, and (3) a second end having a second zone comprising an immobilized antigen which specifically binds to the second analyte;

(b) a second opposable component having (1) an absorber which is brought into fluid communication with an area of the at least one chromatographic medium between the first and second zones thereof when the first and second opposable components are brought into physical contact, and (2) a second applicator impregnated with a labeled specific binding partner for the second analyte which is brought into fluid communication with the second zone when the first and second opposable components are brought into physical contact;

wherein the first and second opposable components are capable of being brought into physical contact to provide a unidirectional chromatographic specific binding assay for the first analyte and a bidirectional chromatographic specific binding assay for the second analyte by physically contacting the absorber to the first opposable component after migration of an applied aqueous sample from the first end to the second end of the first opposable component in order to reverse fluid flow direction between the first and second ends, and detecting the first and second analytes by detecting formation of labeled ternary complexes in the first and second zones, respectively; and, wherein the absorber substantially excludes the labeled specific binding partner to the second analyte from the first zone by blocking the labeled specific binding partner to the second analyte from migrating into the first zone.

4. An assay device for detecting at least two analytes in an aqueous sample, a first analyte that is an antigen and a second analyte that is an antibody, the assay device comprising:

(a) a first opposable component comprising
(i) at least one chromatographic medium having (1) a first end, (2) an intermediate first zone comprising an immobilized specific binding partner to the first analyte, and (3) a second end having a second zone comprising an immobilized antigen which specifically binds to the second analyte, and
(ii) a sample preparation zone located between the first zone and the second zone; and, (b) a second opposable component having (1) a first applicator impregnated with a labeled specific binding partner for the first analyte which is brought into fluid communication with the first zone when the first and second opposable components are brought into physical contact, (2) an absorber which is brought into fluid communication with an area of the at least one chromatographic medium between the first and second zones thereof when the first and second opposable components are brought into physical contact; and (3) a second applicator impregnated with a labeled specific binding partner for the second analyte which is brought into fluid communication with the second zone, when the first and second opposable components are brought into physical contact;

wherein the first and second opposable components are capable of being brought into physical contact to provide a unidirectional chromatographic specific binding assay for the first analyte and a bidirectional chromatographic specific binding assay for the second analyte by physically contacting the absorber to the first opposable component after migration of an applied aqueous sample from the first end to the second end of the first opposable component in order to reverse fluid flow direction between the first and second ends, and detecting the first and second analytes by detecting formation of labeled ternary complexes in the first and second zones, respectively; and, wherein physical contacting of the absorber divides the first zone from the second zone so that the labeled specific binding partner to the second analyte is substantially excluded from the first zone by blocking the labeled specific binding partner to the second analyte from flowing into the first zone.

5. An assay device for detecting at least two analytes in an aqueous sample, a first analyte that is an antigen and a second analyte that is an antibody, the assay device comprising:

(a) a first opposable component comprising
(i) at least one chromatographic medium having in order of fluid communication (1) a first end, (2) a first applicator, (3) a conjugate zone impregnated with a labeled specific binding partner to the first analyte bridging the first end and the first applicator, (4) a first zone comprising an immobilized specific binding partner to the first analyte, (5) a second zone comprising an immobilized antigen which specifically binds to the second analyte, (6) a fluid conductor, and (7) a second end;

(b) a second opposable component comprising
(i) an absorber which is brought into fluid communication with an area of the at least one chromatographic medium between the first and second zones thereof when the first and second opposable components are brought into physical contact; and (ii) a second applicator impregnated with a labeled specific binding partner for the second analyte which is brought into fluid communication with the fluid conductor, when the first and second opposable components are brought into physical contact;

wherein the first and second opposable components are capable of being brought into physical contact to provide a unidirectional chromatographic specific binding assay for the first analyte and a bidirectional chromatographic specific binding assay for the second analyte by physically contacting the absorber to the first opposable component after migration of an applied aqueous sample from the first end to the second end of the first opposable component in order to reverse fluid flow direction between the first and second ends, and detecting the first and second analytes by detecting formation of labeled ternary complexes in the first and second zones, respectively.

6. The assay device of claim 5 wherein the second analyte is an antibody produced by a mammalian species in response to an antigen, wherein the antigen is the same as the immobilized antigen, and the labeled specific binding partner is a labeled antibody that specifically binds to the second analyte by binding to the constant region the second analyte.

7. The assay device of claim 6 wherein the labeled antibody binds the second analyte by binding to a species-specific determinant.

8. The assay device of claim 5 wherein the first and second zones of the at least one chromatographic medium are of differing porosities.

9. The assay device of claim 5 wherein the at least one chromatographic medium is nitrocellulose.

10. A method for determining the presence or amount of at least two analytes in an aqueous sample, comprising the sequential steps of:

(a) applying a first aliquot of the sample to the first applicator of the assay device of claim 5;

(b) allowing the sample to migrate from the first applicator through the conjugate zone and then through at least the fluid conductor of the at least one chromatographic medium so that a first ternary complex is formed in the first zone if the first analyte is present in the sample, the first ternary complex comprising the first analyte, the labeled specific binding partner to the first analyte, and the immobilized specific binding partner to the first analyte;

(c) bringing the first and second opposable components into physical contact to cause the second applicator to come into fluid communication with the at least one chromatographic medium to draw fluid from the second applicator through the fluid conductor and through the second zone of the at least one chromatographic medium from the fluid conductor to the absorber so that a second ternary complex is formed in the second zone if the second analyte is present in the sample, the second ternary complex comprising the second analyte, the labeled specific binding partner to the second analyte, and the immobilized antigen to the second analyte; and, (d) determining the presence or amount of the at least two analytes in the aqueous sample by observing and/or measuring any detectable signal produced by the labeled specific binding partner to at first analyte bound in the first ternary complex in the first zone and any detectable signal produced by the labeled specific binding partner to the second analyte bound in the second ternary complex in the second zone.

11. The method of claim 10 wherein the labeled specific binding partner for the first analyte and the labeled specific binding partner to the second analyte each is labeled with a visually detectable label and the step of observing and/or measuring the detectable signals is performed visually.

12. An assay device for detecting at least two analytes in an aqueous sample, a first analyte that is an antigen and a second analyte that is an antibody, the assay device comprising:

(a) a first opposable component comprising
  (i) at least one chromatographic medium having in order of fluid communication (1) a first end, (2) a first fluid conductor, (3) a sample preparation zone, (4) a first zone comprising an immobilized specific binding partner to the first analyte, (5) a second zone comprising an immobilized antigen which specifically binds to the second analyte, (6) a second fluid conductor, and (7) a second end;

(b) a second opposable component comprising
  (i) a first applicator impregnated with a resolubilizable labeled specific binding partner for the first analyte which is brought into fluid communication with the first fluid conductor when the first and second opposable components are brought into physical contact,
  (ii) an absorber which is brought into fluid communication with the sample preparation zone of the at least one chromatographic medium when the first and second opposable components are brought into physical contact, and
  (iii) a second applicator impregnated with a resolubilizable labeled specific binding partner for the first analyte which is brought into fluid communication with the first fluid conductor, when the first and second opposable components are brought into physical contact;

wherein the first and second opposable components are capable of being brought into physical contact to provide a unidirectional chromatographic specific binding assay for the first analyte and a bidirectional chromatographic specific binding assay for the second analyte by physically contacting the absorber to the first opposable component after migration of an applied aqueous sample from the first end to the second end of the first opposable component in order to reverse fluid flow direction between the first and second ends, and detecting the first and second analytes by detecting formation of labeled ternary complexes in the first and second zones, respectively.

13. The assay device of claim 12 wherein the second analyte is an antibody produced by a mammalian species in response to an antigen, wherein the antigen is the same as the immobilized antigen, and the labeled specific binding partner is a labeled antibody that specifically binds to the second analyte by binding to the constant region the second analyte.

14. The assay device of claim 13 wherein the labeled antibody binds the second analyte by binding to a species-specific determinant.

15. The assay device of claim 12 wherein the first and second zones of the at least one chromatographic medium are of different porosities.

16. The assay device of claim 15 wherein the chromatographic medium is nitrocellulose.

17. A method for determining the presence or amount of at least two analytes in an aqueous sample, comprising the sequential steps of:

(a) applying a first aqueous liquid to the second applicator of the assay device of claim 12 to resolubilized the labeled specific binding partner to the second analyte;

(b) applying a first aliquot of the sample to the first applicator to resolubilize the labeled specific binding partner to the first analyte;

(c) applying a second aliquot of the sample to the sample preparation zone;

(d) allowing the second aliquot of the sample applied to the sample preparation zone to migrate through at least the second fluid conductor of at least one chromatographic medium;

(e) bringing the first and second opposable components into physical contact to cause the absorber to come into contact with the at least one chromatographic medium, the first applicator to come into contact with the first fluid conductor, and the second applicator to come into contact with the second fluid conductor;

(f) allowing the first aliquot of the sample and the resolubilized labeled specific binding partner to the first analyte to migrate through at least the first zone of the at least one chromatographic medium so that a first ternary complex is formed in the first zone if the first analyte is present in the sample, the first ternary complex comprising the first analyte, the labeled specific binding partner to the first analyte, and the immobilized specific binding partner to the first analyte; and, allowing the resolubilized labeled specific binding partner to the second analyte to migrate through at least the second zone of the at least one chromatographic medium so that a second ternary complex is formed in the second zone of the second analyte is present in the sample, the second ternary complex comprising the second analyte, the labeled specific binding partner to the second analyte, and the immobilized antigen to the second analyte; and (g) determining the presence or amount of the first analyte and the second analyte in the aqueous sample by observing and/or measuring any detectable signal produced by the labeled specific binding partner to the first analyte bound in the first ternary complex in the first zone and any detectable signal produced by the labeled specific binding partner to the second analyte bound in the second ternary complex in the second zone.

18. The method of claim 17 wherein the labeled specific binding partner for the first analyte and the labeled specific binding partner to the second analyte are each labeled with a visually detectable label and the step of observing and/or measuring the detectable signals is performed visually.

19. An assay device for detecting at least two analytes in an aqueous sample, a first analyte that is an antigen and a second analyte that is an antibody, the assay device comprising:

(a) a first opposable component comprising
  (i) a first chromatographic medium having in order of fluid communication (1) a first end, (2) a first fluid conductor, (3) a first zone comprising an immobilized specific binding partner to the first analyte, and (4) a second end;
  (ii) a second chromatographic medium having in order of fluid communication (1) a first end, (2) a sample preparation zone, (3) a second zone comprising an immobilized antigen which specifically binds to the second analyte, (4) a second fluid conductor, and (5) a second end;

(b) a second opposable component comprising
  (i) a first applicator impregnated with a resolubilizable labeled specific binding partner for the first analyte which is brought into fluid communication with the first fluid conductor when the first and second opposable components are brought into physical contact,
  (ii) an absorber which is brought into fluid communication with the sample preparation zone of the at least one chromatographic medium when the first and second opposable components are brought into physical contact, and
  (iii) a second applicator impregnated with a resolubilizable labeled specific binding partner for the first analyte which is brought into fluid communication with the first fluid conductor, when the first and second opposable components are brought into physical contact;

wherein the first and second opposable components are capable of being brought into physical contact to provide a unidirectional chromatographic specific binding assay for the first analyte and a bidirectional chromatographic specific binding assay for the second analyte by physically contacting the absorber to the first opposable component after migration of an applied aqueous sample from the first end to the second end of the first opposable component in order to reverse fluid flow direction between the first and second ends, and detecting the first and second analytes by detecting formation of labeled ternary complexes in the first and second zones, respectively.

20. The assay device of claim 19 wherein the second analyte is an antibody produced by a mammalian species in response to an antigen, wherein the antigen is the same as the immobilized antigen, and the labeled specific binding partner is a labeled antibody that specifically binds to the second analyte by binding to the constant region the second analyte.

21. The assay device of claim 20 wherein the labeled antibody binds the second analyte by binding to a species-specific determinant.

22. The assay device of claim 19 wherein the first and second chromatographic media are of differing porosities.

23. The assay device of claim 22 wherein the first and second chromatographic media are each nitrocellulose.

24. A method for determining the presence or amount of at least two analytes simultaneously in an aqueous sample, comprising the sequential steps of:

(a) applying a first aqueous liquid to the second applicator of the assay device of claim 19 to resolubilize the labeled specific binding partner to the second analyte;

(b) applying a first aliquot of the sample to the first applicator of the assay device to resolubilize the labeled specific binding partner to the first analyte;

(c) applying a second aliquot of the sample to the sample preparation zone;

(d) allowing the second aliquot of the sample applied to the sample preparation zone to migrate through at least the second fluid conductor of the second chromatographic medium;

(e) bringing the first and second opposable components into physical contact to cause the absorber to come into contact with the sample preparation zone and the first chromatographic medium, to cause the first applicator to come into contact with the first fluid conductor, and to cause the second applicator to come into contact with the second fluid conductor;

(f) allowing the first aliquot of the sample and the resolubilized labeled specific binding partner to the first analyte to migrate through at least the first zone of the first chromatographic medium and allowing the resolubilized labeled specific binding partner to the second analyte to migrate through at least the second zone of the second chromatographic medium so that a first ternary complex is formed in the first zone of the first chromatographic medium if the first analyte is present in the sample, the first ternary complex comprising the first analyte, the labeled specific binding partner to the first analyte, and the immobilized specific binding partner to the first analyte; and, so that a second ternary complex is formed in second zone of the second chromatographic medium if the second analyte is present in the sample, the second ternary complex comprising the second analyte, the labeled specific binding partner to the second analyte, and the immobilized antigen to the second analyte; and (g) determining the presence or amount of the first analyte and the second analyte in the aqueous sample by observing and/or measuring any detectable signal produced by the labeled specific binding partner to the first analyte bound in the first ternary complex in the first zone in the first chromatographic medium and any detectable signal produced by the labeled specific binding partner to the second analyte bound in the second ternary complex in the second zone of the chromatographic medium.

25. The method of claim 24 wherein the labeled specific binding partner for the first analyte and the labeled specific binding partner to the second analyte are each labeled with a visually detectable label and the step of observing and/or measuring the detectable signals is performed visually.

* * * * *

UNITED STATES PATENT AND TRADEMARK OFFICE
CERTIFICATE OF CORRECTION

PATENT NO. : 5,468,648

DATED : November 21, 1995

INVENTOR(S) : Chandler

It is certified that error appears in the above-identified patent and that said Letters Patent is hereby corrected as shown below:

```
Column 12, line 1, "flow" should read --flows--

Column 18, line 3, "0" should read --40--

Column 18, line 48, "conduct" should read --contact--

Column 18, line 67, "component" should read --components--

Column 21, line 20, "second" should read --seconds--

Column  26, lines 2 & 45, "Triton® X-100" should read --TRITON® X-100--

Column 27, line 46, "each" should read --such--

Column 29, lines 47 & 48, "applied aqueous sample from the first end" should read --aqueous sample applied to the first applicator--

Column 31, line 57, "at" should read --the--

Column 32, lines 25 & 27, "first" should read --second--
```

UNITED STATES PATENT AND TRADEMARK OFFICE
CERTIFICATE OF CORRECTION

PATENT NO. : 5,468,648

DATED : November 21, 1995

INVENTOR(S) : Chandler

It is certified that error appears in the above-identified patent and that said Letters Patent is hereby corrected as shown below:

```
    Column 33, line 67, to column 34, line 1, "of the at least
one" should read --and with the first--

Column 34, lines 5 & 7, "first" should read --second--
```

Signed and Sealed this

Seventeenth Day of March, 1998

*Attest:*

BRUCE LEHMAN

*Attesting Officer*     *Commissioner of Patents and Trademarks*